(12) United States Patent
Biffi et al.

(10) Patent No.: US 11,548,936 B2
(45) Date of Patent: Jan. 10, 2023

(54) COMPOSITIONS AND METHODS FOR TREATING LYSOSOMAL STORAGE DISEASES AND DISORDERS

(71) Applicants: CHILDREN'S MEDICAL CENTER CORPORATION, Boston, MA (US); OSPEDALE SAN RAFFAELE S.R.L., Milan (IT); DANA-FARBER CANCER INSTITUTE, INC., Boston, MA (US); FONDAZIONE TELETHON, Rome (IT)

(72) Inventors: Alessandra Biffi, Boston, MA (US); Eleonora Cavalca, Milan (IT)

(73) Assignees: CHILDREN'S MEDICAL CENTER CORPORATION, Boston, MA (US); OSPEDALE SAN RAFFAELE S.R.L., Milan (IT); DANA-FARBER CANCER INSTITUTE, INC., Boston, MA (US); FONDAZIONE TELETHON, Rome (IT)

( * ) Notice: Subject to any disclaimer, the term of this patent is extended or adjusted under 35 U.S.C. 154(b) by 559 days.

(21) Appl. No.: 16/477,829

(22) PCT Filed: Jan. 16, 2018

(86) PCT No.: PCT/US2018/013909
§ 371 (c)(1),
(2) Date: Jul. 12, 2019

(87) PCT Pub. No.: WO2018/136435
PCT Pub. Date: Jul. 26, 2018

(65) Prior Publication Data
US 2019/0367584 A1    Dec. 5, 2019

Related U.S. Application Data

(60) Provisional application No. 62/582,247, filed on Nov. 6, 2017, provisional application No. 62/447,341, filed on Jan. 17, 2017.

(51) Int. Cl.
*C07K 14/825* (2006.01)
*G01N 33/68* (2006.01)

(52) U.S. Cl.
CPC ....... *C07K 14/825* (2013.01); *G01N 33/6893* (2013.01); *G01N 2333/825* (2013.01); *G01N 2800/04* (2013.01)

(58) Field of Classification Search
CPC .... C07K 14/825; A61K 35/28; A61K 48/005; C12N 2740/16043; G01N 2333/825
See application file for complete search history.

(56) References Cited

U.S. PATENT DOCUMENTS 6,537,785 B1   3/2003   Canfield
8,093,209 B2   1/2012   Laskowitz et al.
(Continued)

FOREIGN PATENT DOCUMENTS

JP    2008534529 A    8/2008
KR    101625755 B1    5/2016
(Continued)

OTHER PUBLICATIONS

"Lysosomal storage diseases" downloaded from Lysosomal storage disease—Wikipedia on Feb. 22, 2022.*
(Continued)

*Primary Examiner* — Terra C Gibbs
(74) *Attorney, Agent, or Firm* — Melissa Hunter-Ensor; Greenberg Traurig, LLP

(57) ABSTRACT

The present invention provides compositions and methods for the treatment or prevention of a lysosomal disease or disorder involving increasing the level, expression, or activity of a metallothionein polypeptide or polynucleotide in the subject.

11 Claims, 24 Drawing Sheets

A

B

(56) References Cited

U.S. PATENT DOCUMENTS

| | | |
|---|---|---|
| 9,339,512 B2 | 5/2016 | Widdowson et al. |
| 2001/0038836 A1 | 11/2001 | During et al. |
| 2004/0067500 A1 | 4/2004 | Gould-Rothberg et al. |
| 2008/0254017 A1 | 10/2008 | Kane et al. |
| 2009/0318333 A1 | 12/2009 | Vallee |
| 2010/0151573 A1 | 6/2010 | King et al. |
| 2010/0166759 A1 | 7/2010 | Berezin et al. |
| 2010/0221225 A1 | 9/2010 | Byrne et al. |
| 2011/0223127 A1 | 9/2011 | Purschke et al. |
| 2014/0235697 A1 | 8/2014 | Weiner et al. |
| 2015/0223436 A1 | 8/2015 | Rossi et al. |
| 2016/0256492 A1 | 9/2016 | Naldini et al. |
| 2017/0333527 A1 | 11/2017 | Fukuta et al. |
| 2018/0161357 A1 | 6/2018 | Jackson et al. |
| 2018/0187156 A1 | 7/2018 | Rossi et al. |
| 2020/0038439 A1 | 2/2020 | Biffi et al. |
| 2020/0278356 A1 | 9/2020 | Biffi et al. |

FOREIGN PATENT DOCUMENTS

| | | |
|---|---|---|
| WO | 1996002670 A1 | 2/1996 |
| WO | 2000029846 A2 | 5/2000 |
| WO | 2002096439 A1 | 12/2002 |
| WO | 2004015089 A1 | 2/2004 |
| WO | 2006102933 A1 | 10/2006 |
| WO | 2010012667 A1 | 2/2010 |
| WO | 2013030785 A1 | 3/2013 |
| WO | 2015164750 A2 | 10/2015 |
| WO | 2016039163 A1 | 3/2016 |
| WO | 2016094880 A1 | 6/2016 |

OTHER PUBLICATIONS

Biffi et al. (Human Molecular Genetics, 2011 vol. 20:R42-R53).*

Cavalca et al. (Ann Neurol., 2018 vol. 83:418-432).*

Cesani, et al., "Metallothioneins as Dynamic Markers for Brain Disease in Lysosomal Disorders," Annals of Neurology, Feb. 12, 2014, vol. 71, No. 1, pp. 127-137.

Kimura, et al., "Function of Metallothionein in Gene Expression and Signal Transduction; Newly Found Protective Role of Metallothionein," Journal of Health Science, Jun. 1, 2008, vol. 54, Issue 3, pp. 251-260.

International Search Report and Written Opinion for corresponding PCT Patent Application PCT/US2018/013909, dated May 8, 2018 (11 pages).

Aronovich et al., "Lysosomal storage disease: Gene therapy on both sides of the blood-brain bar," Molecular Genetics and Metabolism, Feb. 2015, vol. 114, No. 2, pp. 83-93.

Biffi et al., "Lentiviral Hematopoietic Stem Cell Gene Therapy Benefits Metachromatic Leukodystrophy," Science, American Association for the Advancement of Science, US, Jan. 1, 2013, pp. 1233158-1; DOI: 10.1126/SCIENCE.1233158 (retrieved on Jul. 11, 2013).

Sessa et al., "Lentiviral haemopoietic stem-cell gene therapy in early-onset metachromatic leukodystrophy: an ad-hoc analysis of a non-randomised, open-label, phase 1/2 trial," The Lancet, Elsevier, Amsterdam, NL, Jun. 8, 2016, vol. 388, No. 10043, pp. 476-487.

Extended European Search Report issued in corresponding European Patent Application No. 18741761.3, dated Jun. 19, 2020 (9 pages).

Magi et al., "Apolipoprotein E Is a Ligand for Triggering Receptor Expressed on Myeloid Cells 2 (TREM2)," Journal of Biological Chemistry, Oct. 23, 2015, vol. 290, No. 43, pp. 26043-26050.

Qi et al., "Myricitrin Modulates NADPH Oxidase-Dependent ROS Production to Inhibit Endotoxin-Mediated Inflammation by Blocking the JAK/STAT1 and NOX2/p47phox Pathways," Oxidative Medicine and Cellular Longevity, Jun. 20, 2017, vol. 2017, Article ID 9738745, pp. 1-20.

Yu et al., "Metallothionein III is reduced in Alzheimer's disease," Brain Research, Mar. 9, 2001, vol. 894, No. 1, pp. 37-45.

International Search Report and Written Opinion issued in International Patent Application No. PCT/US20/53826, dated Feb. 9, 2021 (18 pages).

International Search Report and Written Opinion issued in International Patent Application No. PCT/US20/53824, dated Mar. 22, 2021 (21 pages).

Kemp et al., "ABCD1 Mutations and the X-linked Adrenoleukodystrophy Mutation Database: Role in Diagnosis and Clinical Correlations," Human Mutation, 2001, vol. 18, pp. 499-515.

Kemper et al., "Newborn screening for X-linked adrenoleukodystrophy: evidence summary and advisory committee recommendation," Genetics in Medicine, Jan. 2017, vol. 19, No. 1, pp. 121-126.

Kuo et al., "Theoretical and practical applications of the intracerebroventricular route for CSF sampling and drug administration in CNS drug discovery research: A mini review," Journal of Neuroscience Methods, 2014, vol. 233, pp. 166-171.

Layre et al., "Novel composite core-shell nanoparticles as busulfan carriers," Journal of Controlled Release, 2006, vol. 111, No. 3, pp. 271-280.

Lin et al., "Mitigation of cerebellar neuropathy in globoid cell leukodystrophy mice by AAV-mediated gene therapy," Gene, 2015, vol. 571, No. 1, pp. 81-90.

MaCauley et al., "Cerebellar Pathology and Motor Deficits in the Palmitoyl Protein Thioesterase 1-Deficient Mouse," Experimental Neurology, May 2009, vol. 217, No. 1, pp. 124-135.

Manso et al., "Overexpression of Metallothionein-1 Modulates the Phenotype of the Tg2576 Mouse Model of Alzheimer's Disease," Journal of Alzheimer's Disease, 2016, vol. 51, No. 1, pp. 81-95.

Matcovitch-Natan et al., "Microglia development follows a stepwise program to regulate brain homeostasis," Science, Aug. 19, 2016, vol. 353, No. 6301, p. 789, aad8670 pp. 1-12.

Matzner et al., "Enzyme replacement improves nervous system pathology and function in a mouse model for metachromatic leukodystrophy," Human Molecular Genetics, 2005, vol. 14, No. 9, pp. 1139-1152.

Mildner et al., "Microglia in the adult brain arise from Ly-6ChiCCR2+ monocytes only under defined host conditions," Nature Neuroscience, Dec. 2007, vol. 10, No. 12, pp. 1544-1553.

Miller et al., "Outcomes after allogeneic hematopoietic cell transplantation for childhood cerebral adrenoleukodystrophy: the largest single-institution cohort report," Blood, Aug. 18, 2011, vol. 118, No. 7, pp. 1971-1978.

Miyamoto et al., "Microglia and synapse interactions: fine tuning neural circuits and candidate molecules," Frontiers in Cellular Neuroscience, May 15, 2013, vol. 7, Article No. 70, pp. 1-6.

Moser, Hugo W., "Adrenoleukodystrophy: phenotype, genetics, pathogenesis and therapy," Brain, Aug. 1997, vol. 120, No. 8, pp. 1485-1508.

Musolino et al., "Hematopoietic Stem Cell Transplantation in the Leukodystrophies: A Systematic Review of the Literature," Neuropediatrics, Jun. 2014, vol. 45, No. 3, pp. 169-174.

Nakao et al., "Atypical expression of circadian clock genes in denervated mouse skeletal muscle," Chronobiology International, 2015, vol. 32, No. 4, pp. 486-496.

Nicaise et al., "A Microglial Hypothesis of Globoid Cell Leukodystrophy Pathology," Journal of Neuroscience Research, Nov. 2016, vol. 94, No. 11, pp. 1049-1061.

Ohmi et al., "Activated microglia in cortex of mouse models of mucopolysaccharidoses I and IIIB," Proceedings of the National Academy of Sciences of the United States of America, Feb. 18, 2003, vol. 100, No. 4, pp. 1902-1907.

Pachiappan et al., "Glial inflammation and neurodegeneration induced by candoxin, a novel neurotoxin from Bungarus candidus venom: global gene expression analysis using microarray," Toxicon, 2005, vol. 46, No. 8, pp. 883-899.

Palmiter et al., "Distal Regulatory Elements from the Mouse Metallothionein Locus Stimulate Gene Expression in Transgenic Mice," Molecular and Cellular Biology, Sep. 1993, vol. 13, No. 9, pp. 5266-5275.

(56) References Cited

OTHER PUBLICATIONS

Perego et al., "Temporal pattern of expression and colocalization of microglia/macrophage phenotype markers following brain ischemic injury in mice," Journal of Neuroinflammation, 2011, vol. 8, Article No. 174, pp. 1-19.
Peviani et al., "Unraveling the Complexity of Amyotrophic Lateral Sclerosis: Recent Advances from the Transgenic Mutant SOD1 Mice," CNS & Neurological Disorders—Drug Targets, 2010, vol. 9, No. 4, pp. 491-503.
Platt, Frances M., "Sphingolipid lysosomal storage disorders," Nature, Jun. 5, 2014, vol. 510, pp. 68-75.
Rettig et al., "Mobilization of hematopoietic stem and progenitor cells using inhibitors of CXCR4 and VLA-4," Leukemia, 2012, vol. 26, pp. 34-53.
Rojo et al., "Redox Control of Microglial Function: Molecular Mechanisms and Functional Significance," Antioxidants & Redox Signaling, 2014, vol. 21, No. 12, pp. 1766-1801.
Settembre et al., "Signals for the lysosome: a control center for cellular clearance and energy metabolism," Nature Reviews: Molecular Cell Biology, May 2013, vol. 14, No. 5, pp. 283-296.
Sharma et al., "Biomarkers in Parkinson's disease (recent update)," Neurochemistry International, 2013, vol. 63, No. 3, pp. 201-229.
Simard et al., "Bone Marrow-Derived Microglia Play a Critical Role in Restricting Senile Plaque Formation in Alzheimer's Disease," Neuron, Feb. 16, 2006, vol. 49, pp. 489-502.
Subramanian et al., "Gene set enrichment analysis: A knowledge-based approach for interpreting genome-wide expression profiles," Proceedings of the National Academy of Sciences of the United States of America, Oct. 25, 2005, vol. 102, No. 43, pp. 15545-15550.
Sugiyama et al., "Maintenance of the Hematopoietic Stem Cell Pool by CXCL12-CXCR4 Chemokine Signaling in Bone Marrow Stromal Cell Niches," Immunity, Dec. 2006, vol. 25, pp. 977-988.
Tay et al., "Microglia across the lifespan: from origin to function in brain development, plasticity and cognition," The Journal of Physiology, 2017, vol. 595, No. 6, pp. 1929-1945.
Tokuda et al., "Overexpression of metallothionein-I, a copper-regulating protein, attenuates intracellular copper dyshomeostasis and extends lifespan in a mouse model of amyotrophic lateral sclerosis caused by mutant superoxide dismutase-1," Human Molecular Genetics, 2014, vol. 23, No. 5, pp. 1271-1285.
Turner et al., "Evidence of widespread cerebral microglial activation in amyotrophic lateral sclerosis: an [11C](R)-PK11195 positron emission tomography study," Neurobiology of Disease, 2004, vol. 15, pp. 601-609.
Vela et al., "Induction of metallothionein in astrocytes and microglia in the spinal cord from the myelin-deficient jimpy mouse," Brain Research, 1997, vol. 767, pp. 345-355.
Villani et al., "Cytokines, Neurotrophins, and Oxidative Stress in Brain Disease From Mucopolysaccharidosis IIIB," Journal of Neuroscience Research, 2007, vol. 85, No. 3, pp. 612-622.
Visigalli et al., "Gene therapy augments the efficacy of hematopoietic cell transplantation and fully corrects mucopolysaccharidosis type I phenotype in the mouse model," Blood, Dec. 9, 2010, vol. 116, No. 24, pp. 5130-5139.
Visigalli et al., "Monitoring disease evolution and treatment response in lysosomal disorders by the peripheral benzodiazepine receptor ligand PK11195," Neurobiology of Disease, 2009, vol. 34, pp. 51-62.
Wada et al., "Microglial activation precedes acute neurodegeneration in Sandhoff disease and is suppressed by bone marrow transplantation," Proceedings of the National Academy of Sciences of the United States of America, Sep. 26, 2000, vol. 97, No. 20, pp. 10954-10959.
Wang et al., "Metallothionein Inhibits Doxorubicin-Induced Mitochondrial Cytochrome c Release and Caspase-3 Activation in Cardiomyocytes," The Journal of Pharmacology and Experimental Therapeutics, 2001, vol. 298, No. 2, pp. 461-468.
Wang et al., "Translocator protein (Tspo) gene promoter-driven green fluorescent protein synthesis in transgenic mice: an in vivo model to study Tspo transcription," Cell and Tissue Research, Nov. 2012, vol. 350, No. 2, pp. 261-275.
West et al., "Metallothionein in the central nervous system: roles in protection, regeneration and cognition," Neurotoxicology, May 2008, vol. 29, No. 3, pp. 488-502.
Wiesinger et al., "The genetic landscape of X-linked adrenoleukodystrophy: inheritance, mutations, modifier genes, and diagnosis," The Application of Clinical Genetics, 2015, vol. 8, pp. 109-121.
Wilkinson et al., "Busulfan Conditioning Enhances Engraftment of Hematopoietic Donor-derived Cells in the Brain Compared With Irradiation," Molecular Therapy, Apr. 2013, vol. 21, No. 4, pp. 868-876.
Office Action dated Jan. 19, 2022 in corresponding Japanese Patent Application No. 2019-559007 (4 pages).
English translation of the Office Action dated Jan. 19, 2022 in corresponding Japanese Patent Application No. 2019-559007 (4 pages).
Office Action dated Jul. 5, 2022 in corresponding Japanese Patent Application No. 2019-559007 (2 pages).
English translation of the Office Action dated Jul. 5, 2022 in corresponding Japanese Patent Application No. 2019-559007 (2 pages).
Ajami et al., "Infiltrating monocytes trigger EAE progression, but do not contribute to the resident microglia pool," Nature Neuroscience, Sep. 2011, vol. 14, No. 9, pp. 1142-1149.
Ajami et al., "Local self-renewal can sustain CNS microglia maintenance and function throughout adult life," Nature Neuroscience, Dec. 2007, vol. 10, No. 12, pp. 1538-1543.
Ambjorn et al., "Metallothionein and a peptide modeled after metallothionein, EmtinB, induce neuronal differentiation and survival through binding to receptors of the low-density lipoprotein receptor family," Journal of Neurochemistry, 2008, vol. 104, pp. 21-37.
Andrews, Glen K., "Regulation of Metallothionein Gene Expression by Oxidative Stress and Metal Ions," Biochemical Pharmacology, 2000, vol. 59, pp. 95-104.
Arnal et al., "Clinical utility of copper, ceruloplasmin, and metallothionein plasma determinations in human neurodegenerative patients and their first-degree relatives," Brain Research, Mar. 10, 2010, vol. 1319, pp. 118-130.
Aubourg et al., "Reversal of Early Neurologic and Neuroradiologic Manifestations of X-linked Adrenoleukodystrophy by Bone Marrow Transplantation," The New England Journal of Medicine, Jun. 28, 1990, vol. 322, No. 26, pp. 1860-1866.
Baird et al., "Metallothionein protects against oxidative stress-induced lysosomal destabilization," Biochemical Journal, 2006, vol. 394, pp. 275-283.
Banati et al., "Positron emission tomography and functional characterization of a complete PBR/TSPO knockout," Nature Communications, Nov. 19, 2014, vol. 5, Article No. 5452, pp. 1-12.
Bennett et al., "New tools for studying microglia in the mouse and human CNS," Proceedings of the National Academy of Sciences of the United States of America, Feb. 16, 2016, vol. 113, pp. E1738-E1746.
Biffi et al., "Correction of metachromatic leukodystrophy in the mouse model by transplantation of genetically modified hematopoietic stem cells," The Journal of Clinical Investigation, Apr. 2004, vol. 113, No. 8, pp. 1118-1129.
Biffi et al., "Gene therapy of metachromatic leukodystrophy reverses neurological damage and deficits in mice," The Journal of Clinical Investigation, Nov. 2006, vol. 116, No. 11, pp. 3070-3082.
Biffi, Alessandra, "Gene therapy for lysosomal storage disorders: a good start," Human Molecular Genetics, 2016, vol. 25, No. R1, pp. R65-R75.
Butovsky et al., "Identification of a Unique TGF-β Dependent Molecular and Functional Signature in Microglia," Nature Neuroscience, Jan. 2014, vol. 17, No. 1, pp. 131-143.
Cai et al., "Zinc- or cadmium-pre-induced metallothionein protects human central nervous system cells and astrocytes from radiation-induced apoptosis," Toxicology Letters, 2004, vol. 146, No. 3, pp. 217-226.

(56) References Cited

OTHER PUBLICATIONS

Capotondo et al., "Brain conditioning is instrumental for successful microglia reconstitution following hematopoietic stem cell transplantation," Proceedings of the National Academy of Sciences of the United States of America, Sep. 11, 2012, vol. 109, No. 37, pp. 15018-15023.
Cartier et al., "Hematopoietic Stem Cell Gene Therapy with a Lentiviral Vector in X-Linked Adrenoleukodystrophy," Science, Nov. 6, 2009, vol. 326, pp. 818-823.
Cartier et al., "Hematopoietic Stem Cell Transplantation and Hematopoietic Stem Cell Gene Therapy in X-Linked Adrenoleukodystrophy," Brain Pathology, 2010, vol. 20, No. 4, pp. 857-862.
Cesani et al., "Characterization of New Arylsulfatase A Gene Mutations Reinforces Genotype-Phenotype Correlation in Metachromatic Leukodystrophy," Human Mutation, 2009, vol. 30, pp. E936-E945.
Chimienti et al., "Zinc resistance impairs sensitivity to oxidative stress in hela cells: protection through metallothioneins expression," Free Radical Biology & Medicine, 2001, vol. 31, No. 10, pp. 1179-1190.
Chiu et al., "A Neurodegeneration-Specific Gene-Expression Signature of Acutely Isolated Microglia from an Amyotrophic Lateral Sclerosis Mouse Model," Cell Reports, Jul. 25, 2013, vol. 4, pp. 385-401.
Chung et al., "New insight into the molecular pathways of metallothionein-mediated neuroprotection and regeneration," Journal of Neurochemistry, 2008, vol. 104, pp. 14-20.
Chung et al., "Redefining the Role of Metallothionein within the Injured Brain: Extracellular Metallothioneins Play an Important Role in the Astrocyte-Neuron Response to Injury," The Journal of Biological Chemistry, May 30, 2008, vol. 283, No. 22, pp. 15349-15358.
ClinicalTrials.gov Identifier: NCT01560182.
ClinicalTrials.gov Identifier: NCT01801709.
ClinicalTrials.gov Identifier: NCT02055118.
ClinicalTrials.gov Identifier: NCT02725580.
Colonna et al., "Microglia Function in the Central Nervous System During Health and Neurodegeneration," Annual Review of Immunology, 2017, vol. 35, pp. 441-468.
Comes et al., "Influence of Transgenic Metallothionein-1 on Gliosis, CA1 Neuronal Loss, and Brain Metal Levels of the Tg2576 Mouse Model of Alzheimer's Disease," International Journal of Molecular Sciences, 2017, vol. 18, Article No. 251, pp. 1-12.
Dar et al., "Mutual, reciprocal SDF-1/CXCR4 interactions between hematopoietic and bone marrow stromal cells regulate human stem cell migration and development in NOD/SCID chimeric mice," Experimental Hematology, 2006, vol. 34, pp. 967-975.
Deverman et al., "Cre-dependent selection yields AAV variants for widespread gene transfer to the adult brain," Nature Biotechnology, Feb. 2016, vol. 34, No. 2, pp. 204-209.
Di Foggia et al., "Bmi1 enhances skeletal muscle regeneration through MT1-mediated oxidative stress protection in a mouse model of dystrophinopathy," Journal of Experimental Medicine, 2014, vol. 211, No. 13, pp. 2617-2633.
Ebadi et al., "Metallothionein-mediated neuroprotection in genetically engineered mouse models of Parkinson's disease," Brain Research: Molecular Brain Research, Mar. 24, 2005, vol. 134, No. 1, pp. 67-75.
Eichler et al., "Hematopoietic Stem-Cell Gene Therapy for Cerebral Adrenoleukodystrophy," The New England Journal of Medicine, Oct. 26, 2017, vol. 377, No. 17, pp. 1630-1638.
Eichler et al., "Is Microglial Apoptosis an Early Pathogenic Change in Cerebral X-Linked Adrenoleukodystrophy?" Annals of Neurology, Jun. 2008, vol. 63, No. 6, pp. 729-742.
Elmore et al., "Colony-Stimulating Factor 1 Receptor Signaling Is Necessary for Microglia Viability, Unmasking a Microglia Progenitor Cell in the Adult Brain," Neuron, Apr. 16, 2014, vol. 82, pp. 380-397.
Engelen et al., "X-linked adrenoleukodystrophy (X-ALD): clinical presentation and guidelines for diagnosis, follow-up and management," Orphanet Journal of Rare Diseases, 2012, vol. 7, Article No. 51, pp. 1-14.
Escolar et al., "Transplantation of Umbilical-Cord Blood in Babies with Infantile Krabbe's Disease," The New England Journal of Medicine, May 19, 2005, vol. 352, No. 20, pp. 2069-2081.
Filippon et al., "Oxidative stress in patients with mucopolysaccharidosis type II before and during enzyme replacement therapy," Molecular Genetics and Metabolism, 2011, vol. 103, No. 2, pp. 121-127.
Futerman et al., "The Cell Biology of Lysosomal Storage Disorders," Nature Reviews: Molecular Cell Biology, Jul. 2004, vol. 5, pp. 554-565.
Gazit et al., "Fgd5 identifies hematopoietic stem cells in the murine bone marrow," The Journal of Experimental Medicine, 2014, vol. 211, No. 7, pp. 1315-1331.
Gentner et al., "Identification of Hematopoietic Stem Cell-Specific miRNAs Enables Gene Therapy of Globoid Cell Leukodystrophy," Science Translational Medicine, Nov. 17, 2010, vol. 2, No. 58, 58ra84, pp. 1-11, supplemental pp. 1-22.
Ginhoux et al., "Fate Mapping Analysis Reveals That Adult Microglia Derive from Primitive Macrophages," Science, Nov. 5, 2010, vol. 330, No. 6005, pp. 841-845.
Gosselin et al., "Environment Drives Selection and Function of Enhancers Controlling Tissue-Specific Macrophage Identities," Cell, Dec. 4, 2014, vol. 159, pp. 1327-1340.
Grommes et al., "Regulation of Microglial Phagocytosis and Inflammatory Gene Expression by Gas6 Acting on the Axl/Mer Family of Tyrosine Kinases," Journal of Neuroimmune Pharmacology, Jun. 2008, vol. 3, No. 2, pp. 130-140.
Hennecke et al., "RNA biomarkers of Parkinson's disease: developing tools for novel therapies," Biomarkers in Medicine, 2008, vol. 2, No. 1, pp. 41-53.
Hickman et al., "The Microglial Sensome Revealed by Direct RNA Sequencing," Nature Neuroscience, Dec. 2013, vol. 16, No. 12, pp. 1896-1905.
Hidalgo et al., "Expression of Metallothionein-I, -II, and -III in Alzheimer Disease and Animal Models of Neuroinflammation," Experimental Biology and Medicine, 2006, vol. 231, No. 9, pp. 1450-1458.
Hu et al., "Hematopoietic Stem Cell Transplantation and Lentiviral Vector-Based Gene Therapy for Krabbe's Disease: Present Convictions and Future Prospects," Journal of Neuroscience Research, 2016, vol. 94, pp. 1152-1168.
Ito et al., "The Potential Roles of Metallothionein as a Therapeutic Target for Cerebral Ischemia and Retinal Diseases," Current Pharmaceutical Biotechnology, 2013, vol. 14, No. 4, pp. 400-407.
Jeyakumar et al., "Central nervous system inflammation is a hallmark of pathogenesis in mouse models of GM1 and GM2 gangliosidosis," Brain, 2003, vol. 126, pp. 974-987.
Examination Report dated Sep. 8, 2022 in corresponding Australian Patent Application No. 2018210853 (4 pages).

* cited by examiner

A

C

K

COMPOSITIONS AND METHODS FOR TREATING LYSOSOMAL STORAGE DISEASES AND DISORDERS

CROSS-REFERENCE TO RELATED APPLICATIONS

This application is the U.S. National Phase application, pursuant to 35 U.S.C. § 371, of PCT International Application Serial No.: PCT/US2018/013909, filed Jan. 16, 2018, designating the United States and published in English, which claims priority to and the benefit of U.S. Provisional Application Nos. 62/447,341, filed Jan. 17, 2017 and 62/582,247, filed Nov. 6, 2017, respectively, the disclosures of each of which are incorporated herein by reference in its entirety.

BACKGROUND OF THE INVENTION

Most lysosomal storage disorders (LSDs) with central nervous system (CNS) involvement lack an effective and curative treatment and patients eventually succumb to their devastating disease. Frequently, disease onset occurs in very early infancy and is characterized by subtle manifestations, leading to diagnosis in clearly symptomatic if not advanced stage. LSDs are also characterized by a rapid early disease progression, particularly in early onset variants. For these reasons therapeutic approaches that have been applied with some degree of success in pre-symptomatic LSD children, including for example, hematopoietic cell transplantation (HCT) in Krabbe disease, or hematopoietic stem cell (HSC) gene therapy (HSC GT) in Metachromatic Leukodystrophy (MLD), are not beneficial for the majority of LSD patients, with benefit being associated almost exclusively to procedures applied in pre- or early-symptomatic cases. One of the key reasons for the failure of these HSC-based approaches in ameliorating rapidly progressing LSD brain diseases is the slow pace of replacement of resident CNS tissue macrophages/histiocytes and microglia by the transplanted hematopoietic cell progeny, compared to the rapid progression of the primary neurological disease. Indeed, while a rapid reconstitution of visceral organ macrophages by donor-derived cells has been clearly demonstrated following HCT, more limited and slower infiltration of the brain parenchyme by donor cells is supposed to occur. Moreover, efficiency of uptake by different cell types and intrinsic pathologic mechanisms related to enzyme deficiency are not entirely overcome by enzyme replacement and cross correction may account for the residual and long-term progressing disease observed in the transplanted patients. Importantly, in the majority of LSDs lysosomal enzyme deficiency triggers a cascade of events ultimately leading to neuroinflammation, activation of oxidative stress pathways and consequent neurodegeneration. These mechanisms are critically affecting response to treatment and are as well key therapeutic targets for comprehensive approaches. Accordingly, new compositions and methods of treatment are needed for patients afflicted with a lysosomal storage disorder.

SUMMARY

As described below, disclosed herein are compositions and methods for the treatment or prevention of a lysosomal storage disorder (e.g., Neuronal Ceroid Lipofuscinoses) by increasing the level, expression, or activity of a metallothionein polyepeptide or polynucleotide in the subject. In some embodiments, the methods involve replacing a patient's endogenous microglia with either donor derived or engineered cells able to contribute to disease amelioration by different mechanisms, such as protein delivery or regulation of local inflammation and oxidative stress or others.

Thus, In one aspect, disclosed herein are compositions and methods of treating a lysosomal storage disease or disorder in a subject, involving increasing the level, expression, or activity of a metallothionein polyepeptide or polynucleotide in the subject relative to a reference.

In various embodiments of any aspect delineated herein, the lysosomal storage disorder with CNS involvement is Neuronal Ceroid Lipofuscinoses, globoid leukodystrophy, GM1 gangliosidoses, Juvenile Hexosaminidase A Deficiency, Metachromatic Leukodystrophy, Mucopolysaccharidoses disorders, Multiple sulfatase deficiency, Tay-Sachs/GM2 gangliosidosis.

In various embodiments of any aspect delineated herein, the subject is pre-selected by detecting an increase in the level of a metallothionein (MT) polynucleotide or polypeptide in a sample of the subject relative to a reference.

In various embodiments of any aspect delineated herein, the metallothionein is one or more of metallothionein-1A (MT1A), metallothionein-1B (MT1B), metallothionein-1E (MT1E), metallothionein-1F (MT1F), metallothionein-1G (MT1G), metallothionein-1H (MT1H), metallothionein-1I pseudogene (MT1Ip or MTE), metallothionein-1L (LT1L or MT1R), metallothionem-1M (MT1M or MT1K), metallothionein-1X (MT1X), metallothionein-2 (MT2), metallothionein-2A (MT2A), metallothionein-3 (MT3), and metallothionein-4 (MT4).

In various embodiments of any aspect delineated herein, the method involves administering one or more MTs to the subject.

In various embodiments of any aspect delineated herein, the method involves generating in a subject a sustained mixed hematopoietic chimerism in the brain and in the extra-CNS tissues with Hematopoietic Stem Cells (HSCs) encoding one or more MTs. In various embodiments of any aspect delineated herein, the method involves treating a subject having or being at increased risk of developing a lysosomal storage disorder, including by administering a Hematopoietic Stem Cell (HSC) that is one or more of $CD34^+$, $CD38^-$, where the HSC is administered intravenously (IV) or by Intra-cerebral Ventricular (ICV) Injection in combination with ablative conditioning. In various embodiments of any aspect delineated herein, the isolated HSC is transformed with a vector expressing one or more therapeutic polypeptide or polynucleotide, where the HSC is one or more of $CD34^+$, $CD38^-$. In various embodiments, the HSC are engineered with integrating vectors, i.e. lentiviral vectors, to express a one or more methallothioeins +/− a lysosomal enzyme of interest (defective in the target disease). In various embodiments of any aspect delineated herein, the method involves ablating endogenous myeloid cells and microglia and/or their progenitors by a conditioning regimen and reconstituting the microglia by HSC engraftment in a subject. In various embodiments of any aspect delineated herein, the HSC is administered in combination with ablative conditioning. In various embodiments, the ablative conditioning comprises administering a cytotoxic agent to the subject. In various embodiments, the alkylating agent is busulfan. In various embodiments, the ablative conditioning is performed prior to administering the HSC.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

The term "antibody," as used herein, refers to an immunoglobulin molecule which specifically binds with an antigen. The term "antibody fragment" refers to a portion of an intact antibody and refers to the antigenic determining variable regions of an intact antibody.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a protein or nucleic acid that is substantially identical to a reference protein or nucleic acid. In some embodiments the portion retains at least 50%, 75%, or 80%, or more preferably 90%, 95%, or even 99% of the biological activity of the reference protein or nucleic acid described herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein "lysosomal storage disorder (SD)" refers to any of a group of diseases resulting from abnormal metabolism leading to accumulation of a substrate (for example sulfatides, heparan sulphate, glycolipids, ceramide) in the lysosome. For example, lysosomal storage disorders (LSDs) are caused by lysosomal dysfunction usually as a consequence of deficiency of an enzyme required for the metabolism of lipids, glycoproteins (sugar-containing proteins) or so-called mucopolysaccharides.

By "marker" is meant any clinical indicator, protein, metabolite, or polynucleotide having an alteration associated with a disease, disorder, or condition.

By "microglia" is meant an immune cell of the central nervous system.

As used herein "neurodegenerative disease" refers to a disease characterized by the progressive loss of structure and/or function of neurons, including death of neurons.

By "increasing proliferation" is meant increasing cell division of a cell in vivo or in vitro.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "reduces" is meant a negative alteration of at least 10%, 25%, 50%, 75%, or 100%.

By "reference" is meant a standard of comparison or control condition.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "specifically binds" is meant a compound (e.g., peptide) that recognizes and binds a molecule (e.g., polypeptide), but which does not substantially recognize and bind other molecules in a sample, for example, a biological sample.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIG. 1A shows representative pictures of MT immunoreactivity in post-mortem brain samples from GLD, MLD, NPC and NCL patients, as indicated. Grey and white matter (GM and WM) are shown for leukodystrophies, while only GM is shown for NPC and NCL. MT immunoreactivity is primarily associated to astrocytes in both cortex and white matter. Neurons showed MT immunoreactivity in NCL brain samples only (*), while MT positive histiocytes (#) were only observed in MLD. 40× magnification.

FIG. 1B is a graph that provides relative abundance of Lrp2 mRNA in brain of LSDs with neurologic involvement, compared to age-matched normal donor (ND) samples. Mean±SEM. One-way Anova with Bonferroni post-test, **=P value<0.01. GLD n=2, NPC n=3, MLD n=3, NCL n=4, ND=12.

FIG. 1C is a Western blot showing immunoreactivity for megalin/Lrp2 protein on protein extract from 4 LSD brains (GLD n=1, NPC n=1, MLD n=1, NCL n=2) and 3 NDs. α-actin immunoreactivity was assessed as control for protein loading.

FIG. 1D is a graph showing MT1 mRNA expression levels in LSD mouse models. mMT1 levels were measured in the following LSD mouse models: GLD (n=6 at 40 days), MLD (n=4 at 10 months), Sandhoff (SD n=4, 3.5 months), INCL (n=4 at 200 days), MPSI (n=4 at 10 months), MPSII (n=3 at 10 months), MPSIII (n=4 at 40 days), Multiple Sulfatase Deficiency (MSD n=5 at 2-3 weeks), compared to 20 WT mice at different ages. One-way Anova, Dunnett's correction, **=P value<0.01, *=P value<0.05.

FIG. 2A is a graph showing MT brain expression in naïve and MT-transgenic Galc−/− and Ppt1−/− mice. The MT-1 expression levels (MT-1 mRNA abundance) in MTtg (n=8), GLD (n=8), MT-GLD (n=8), INCL (n=5) and MT-INCL (n=5) mice were calculated as fold to WT levels. Mean with SEM. One-way ANOVA with Bonferroni post-test: **=P value<0.01, *=P value<0.05. In both naïve animal disease models MT expression is increased over wild type levels due to reactive disease mechanisms; MT expression further increases upon affected mice crossing with the MT-transgenic line.

FIG. 2B shows representative confocal images of the pons region of a MT-GLD mouse at PND36 stained for astrocytes (GFAP-red), Metallothioneins (MT-green) and DAPI, confirming MT specificity of expression in astrocytes. 20× (left) and 40× (right) magnification.

FIG. 2C shows representative confocal images of the pons region of a GLD and of a MT-GLD mouse at PND36 stained for microglia (IBA-red), Metallothioneins (MT-green) and DAPI, showing few MT-positive cells co-localizing with microglia signal in both animals and more intense MT staining in the MT-GLD sample. 20× magnification.

FIG. 2D and FIG. 2E depict experiments in which an MT1 transgenic (over-expressing) mouse was crossed with either Galc−/− or Ppt1−/− mice, which are animal models of the lysosomal storage diseases globoid cell leukodystrophy (or Krabbe disease) and neuronal ceroid lypofuscinosis 1, respectively. FIG. 2D provides a Kaplan-Meier survival curve of MT-GLD and GLD mice. Data were analyzed by Log-Rank (Mantel-Cox) test; P value<0.0001. FIG. 2E provides a Kaplan-Meier survival curve of MT-INCL and INCL mice. Data are analyzed by Log-Rank (Mantel-Cox) test; P value<0.0001. Survival curves of naïve and MT-transgenic Galc−/− (FIG. 2D) and Ppt1−/− (FIG. 2E) mice were generated showing a survival advantage of the affected transgenic animals (over-expressing MTs) over the not transgenic affected mice.

FIG. 2F is a graph showing Disease Severity Score (DSS) of MT-INCL and INCL mice. INCL, n=10 and MT-INCL, n=10. Two-way ANOVA repeated measures followed by Bonferroni correction: * P value<0.05, *** P value<0.001. Mean disease score in naïve and MT-transgenic Ppt1−/− mice up to 250 days of survival. The disease score accounts for motor function, muscle strength and occurrence of seizures.

FIG. 2G is a graph depicting correlation of survival data of FIG. 2D and MT levels (expressed as fold to WT levels) presented in FIG. 2A, including both GLD and MT-GLD data sets. The figure represents the maximum survival of the natural occurring disease model interpolated with MT expression levels in the same animals, identifying the minimum MT level associated to survival gain. The range of MT levels detected in GLD and MT-GLD mice is here also shown.

FIG. 2H is a graph depicting correlation of survival data of FIG. 2E and MT levels (expressed as fold to WT levels) presented in FIG. 2A, including both INCL and MT-INCL data sets. The figure represents the maximum survival of the natural occurring disease model interpolated with MT expression levels in the same animals, identifying the minimum MT level associated to survival gain. The range of MT levels detected in INCL and MT-INCL mice is here also shown.

FIG. 3A provides a hierarchical clustering representing differentially expressed genes, up-regulated and down-regulated, in the four tested groups. As shown in the bar, over-expression was visualized in shades of red and under-expression in shades of blue. Transcriptome array was performed on cerebellar extracts from the following mice all analyzed at PND36: 3 WT, 3 MTtg, 3 MT-GLD and 3 GLD.

FIG. 3B, FIG. 3C, and FIG. 3D are graphs showing Ifi44 (FIG. 3B), Hpgd (FIG. 3C) and Casp4 (FIG. 3D) expression variations in LSD and MT-LSD brain samples. The left panels of FIG. 3B-FIG. 3C-FIG. 3D show fold expression changes in the indicated pairs, calculated from transcriptome analysis data; fold change of Ifi44 for MT-GLD vs GLD is-2,5528, P value <0.001; fold change of Hpgd for MT-GLD vs GLD is-2,24130, P value <0.001; fold change of Casp4 for MT-GLD vs GLD is-1,75215, P value <0.01. The central and right panels of FIG. 3B, FIG. 3C, and FIG. 3D, Ifi44 (FIG. 3B), Hpgd (FIG. 3C) and Casp4 (FIG. 3D) show relative mRNA abundances calculated by qPCR on MTtg, GLD and MT-GLD mice (central panels) and MT-Tg, INCL and MT-INCL mice (right panels); n=4 mice per group; mean with SEM; analyzed by one Way Anova with Bonferroni post-test, * P value<0.05,  P value<0.01, * P value<0.001. The expression of Casp4 is reduced in the transgenic affected mice as compared to naïve affected controls.

FIG. 3E shows representative pictures of nitrotyrosine (Nitro) staining in brain sections of WT, GLD and MT-GLD mice. Other regions were analyzed with the same expression pattern. All the animals were analyzed at PND36. Magnification 40×.

FIG. 3F is a graph that shows quantification of nitrotyrosine immunopositive area in the CNS (cerebellum, corpus callosum and brainstem analyzed) of GLD (n=3) and MT-GLD (n=3) at PND36, 3 slices per animal, 2 fields per slice, expressed as fold to WT (n=3). Data were analyzed by unpaired t-test comparing MT-GLD vs GLD, *** P value<0.001. Mean with SEM. The expression of nitrotyrosine is reduced in the transigenic affected mice as compared to naïve affected controls.

FIG. 3G includes a graph and histograms showing intracellular reactive oxygen species (ROS) measured by fluorescent dye H2DCFDA incubated with myeloid cells isolated from mouse brains (WT n=5, GLD n=5 and MT-GLD n=5) and analyzed at flow cytometry. FIG. 3G (left panel) shows results presented as % DCFDA positive cells within total live myeloid cells. Mean with SEM. (G right panels) Representative histograms, inclusive of the positive control (Co+, WT cells supplemented with H2O2). The expression of DCDFA is reduced in the trangenic affected mice as compared to naïve affected controls.

FIG. 4A, FIG. 4B, FIG. 4C, FIG. 4D, and FIG. 4E are representative images and graphs showing neuroprotective effect of MT in Galc-/- or Ppt1-/- mice. Cerebellum sections from wild type, and naïve and MT-transgenic Galc-/- (FIG. 4A, FIG. 4B) and Ppt1-/- (FIG. 4C) mice are shown. Purkinje cells are detectable by positive Calbindin (CALB) staining (A) and by their morphological features at crystal violet (C). Purkinje cells were quantified and were shown to be markedly reduced in the diseased animals, but not in the disease MT transgenic mice.

FIG. 4A shows representative pictures of Calbindin staining on slices of the cerebellum of WT, GLD and MT-GLD mice. All the animals were analyzed at PND36.

FIG. 4B is a graph that shows quantification of Calbindin positive cells in WT (n=3), GLD (n=3) and MT-GLD (n=3) mice cerebella at PND36, expressed as number of cells within 100 μm (3 slices per animal, 2 fields per slice). Mean with SEM. Data are analyzed by One-way ANOVA with Bonferroni correction; *** P value<0.001.

FIG. 4C shows representative pictures of Parvalbumin staining in the cerebellum of WT, GLD and MT-GLD at PND36. Nuclei were stained with Topro III.

FIG. 4D is a graph that shows quantification of Parvalbumin positive cells in WT (n=3), GLD (n=3) and MT-GLD (n=3) mice cerebella at PND36, expressed as number of cells within 100 μm (3 slices per animal, 2 fields per slice). Mean with SEM. Data are analyzed by One-way ANOVA with Bonferroni correction; **** P value<0.0001.

FIG. 4E shows representative pictures of Nissl staining to detect Purkinje cells, in the cerebellum of WT, INCL and MT-INCL. All the animals were analyzed at intermediate disease stage of 200 days.

FIG. 4F is a graph that shows a Calbindin count of WT (n=5), INCL (n=5) and MT-INCL (n=5) at PND200, expressed as number of cells within 100 μm (3 slices per animal, 2 fields per slice). Mean with SEM. Data are analyzed by One-way ANOVA with Bonferroni correction; **** P value<0.001.

FIG. 4G is a graph that shows quantification of lectin positive area in the pons region (but the same pattern of expression was detected in other brain regions as cerebellum and corpus callosum) of WT (n=3), GLD (n=3) and MT-GLD (n=3) (3 slices per animal, 2 fields per slice. Data are expressed as ratio to WT levels. Mean with SEM. Data are analyzed by One-way ANOVA with Bonferroni correction.

FIG. 4H is a graph that shows quantification of autofluorescent positive area in different brain regions (cortex, thalamus, hippocampus) of WT (n=5), INCL (n=5) and MT-INCL (n=5) at PND200 (3 slices per animal, 2 fields per slice). Data were expressed as ratio to WT, nuclei were stained with DAPI. Mean with SEM. Data are analyzed by One-way ANOVA with Bonferroni correction.

FIG. 5A shows representative pictures of GFAP staining in the pons region of WT, GLD and MT-GLD. All the animals were analyzed at PND36. 20× magnification.

FIG. 5B is a graph that shows quantification of GFAP-immunopositive area in the pons region of WT (n=3), GLD (n=3) and MT-GLD (n=3) at PND36 (3 slices per animal, 2 fields per slice). For the INCL model the analysis was performed on WT (n=3), INCL (n=5) and MT-INCL (n=5) at PND200 (3 slices per animal and per region, 2 fields per slice from thalamus, cortex and hippocampus). Data are presented as ratio to WT for each model and analyzed by unpaired t-test. Mean with SEM.

FIG. 5C shows representative pictures of IBA staining in the pons region of WT, GLD and MT-GLD. All the animals were analyzed at PND36. 20× magnification.

FIG. 5D is a graph that shows quantification of IBA-immunopositive area in the pons region of WT (n=3), GLD (n=3) and MT-GLD (n=3) at PND36 (3 slices per animal, 2 fields per slice). For the INCL model the analysis was performed on WT (n=3), INCL (n=5) and MT-INCL (n=5) at PND200 (3 slices per animal and per region, 2 fields per slice from thalamus, cortex and hippocampus). Data are presented as ratio to WT for each model and analyzed by unpaired t-test. Mean with SEM.

FIG. 5E, FIG. 5F, FIG. 5G, FIG. 5H, and FIG. 5I are graphs showing the effect of transgenic MT over-expression on microglia phenotype in Galc-/- or Ppt1-/- mice. Microglia cells were sorted from the brain of wild type, naïve affected and MT transgenic affected animals and tested for the expression of the listed genes. Affected naïve animals have a prevalent pro-inflammatory microglia phenotype (IL1β and TNFα increased expression) that is reduced in MT transgenic affected animals. An increase of the expression of markers associated to neuroprotective microglia phenotype (CD206, ARG1, YM1) is also observed in MT transgenic affected animals. The graphs that show the relative abundance of CD206 (FIG. 5E), Arginasel (FIG. 5F), YM1 (FIG. 5G), IL1β (FIG. 5H), TNFα (FIG. SI) mRNAs in total myeloid populations isolated by sorting from the brain of WT (n=6), MTtg (n=3), GLD (n=5) and MT-GLD mice (n=5) at PND36, and from INCL (n=5) and MT-INCL (n=5) mice at PND200. Data are expressed as fold to WT levels, analyzed by One-way ANOVA with Bonferroni correction; ****P value<0.001. Mean with SEM.

FIG. 5J is a graph that shows quantification of CD206-immunopositive area in the pons region of WT (n=3), GLD (n=3) and MT-GLD (n=3) (3 slices per animal, 2 fields per slice). Data are expressed as ratio to WT and analyzed by unpaired t-test comparing MT-GLD vs GLD; ** P value 0.0085.

FIG. 5K shows representative pictures of the pons region of MTtg, GLD and MT-GLD mice showing co-localization of IBA signal with CD206. 40× magnification.

FIG. 6A is a graph that shows relative mRNA abundance of MT1 in HEK293T transduced with AAV-PHP.B (AAV) encoding 1 (AAV-MT) and 4 (AAV-4MT) MT-1 copies in two independent experiments (duplicate) and reported as fold to UT samples One-way ANOVA with Bonferroni correction; * P value<0.05, *** P value<0.001. Mean with SEM.

FIG. 6B is Kaplan-Meier survival curve of GLD mice injected intravenously (IV) with AAV-4MT (IV AAV) (n=7) compared to mice injected with PBS as control (n=5), showing a significant difference between the two groups. Data were analyzed by Log-Rank (Mantel-Cox) test, P value 0.0059.

FIG. 6C is a graph that shows relative mRNA abundance of MT-1 in the brain of MTtg over-expressing transgenic mice (n=8), GLD mice injected with the AAV-4MT vector (IV AAV)(n=7), GLD mice injected with PBS as control (n=5). Mean with SEM.

FIG. 6D is a graph depicting correlation of survival data of FIG. 6B and MT levels measured in the same mice, including both GLD and AAV-GLD data sets. The figure represents the maximum survival of the natural occurring disease model interpolated with MT expression levels in the same animals, identifying the minimum MT level associated to survival gain. The range of MT levels detected in GLD and AAV-GLD mice is here also shown.

FIG. 6E, FIG. 6F, and FIG. 6G include graphs that show relative mRNA abundance of Ifi44 (FIG. 6E), Hpgd (FIG. 6F), and Casp4 (FIG. 6G) in the brain of GLD mice injected IV with AAV-4MT or PBS, reported as fold to WT samples. * P value<0.05 with unpaired t-test. Mean with SEM.

DETAILED DESCRIPTION OF THE INVENTION

Figure 1:
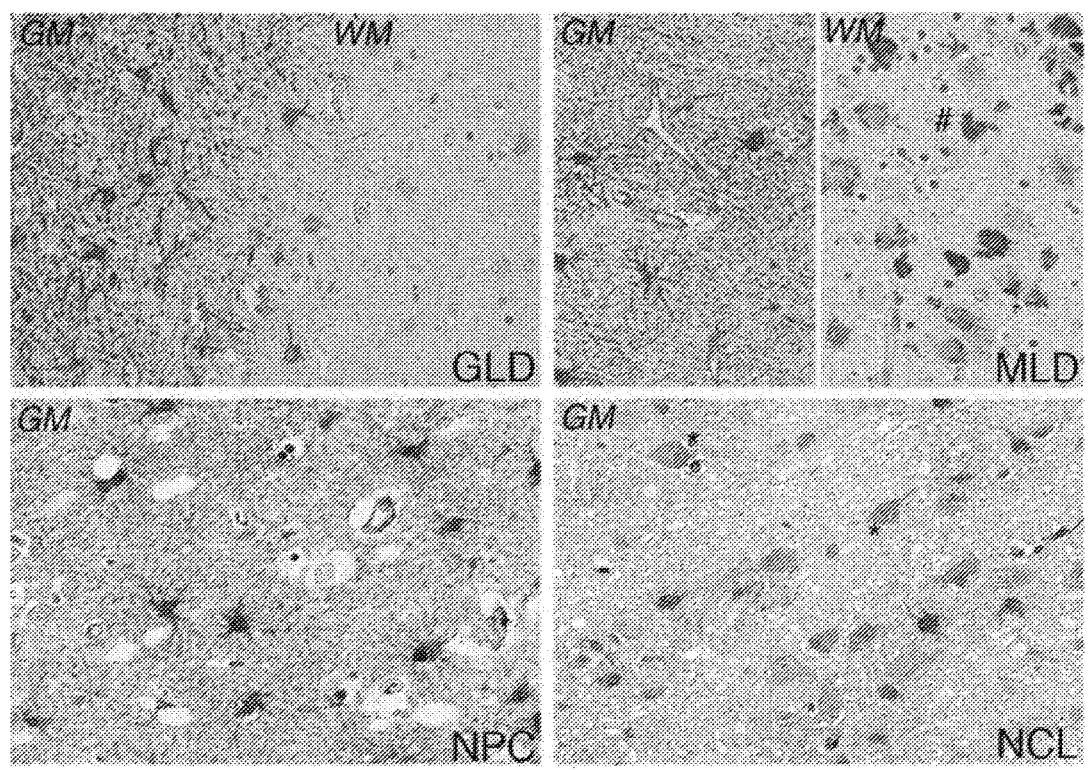
FIG. 1A, FIG. 1B, FIG. 1C and FIG. 1D show disease model selection for preclinical testing of MTs as therapeutic agents in LSDs.
Figure 1:
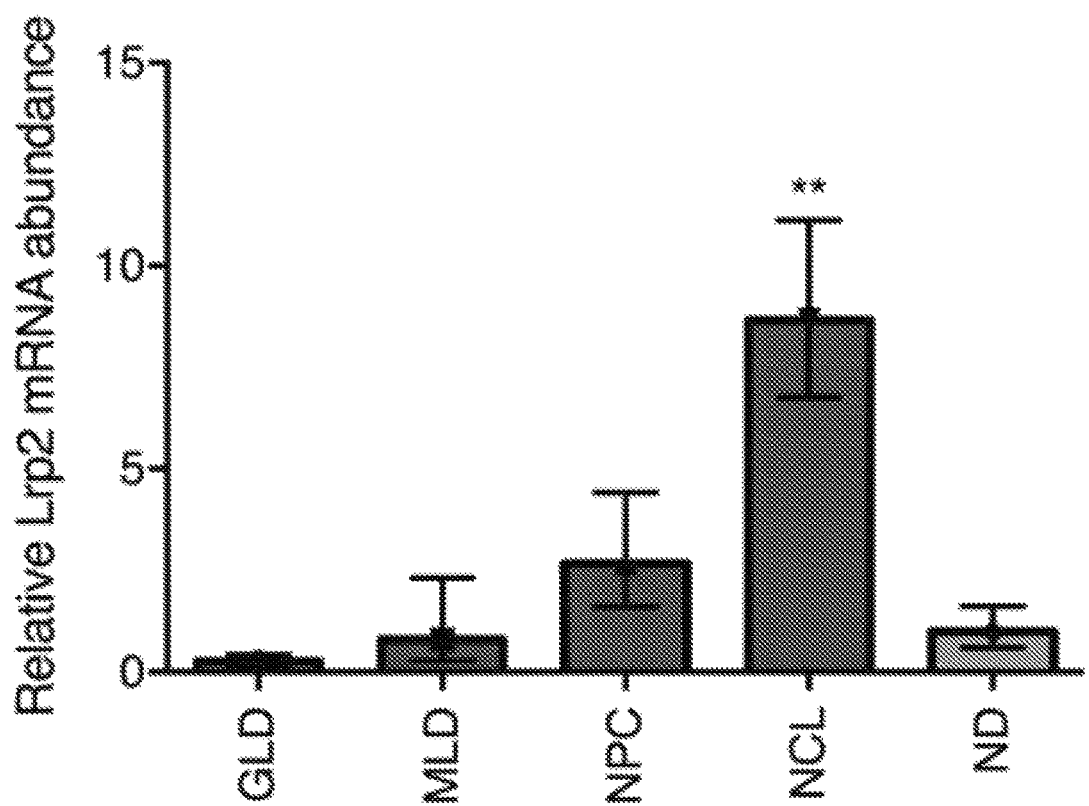
Figure 1:
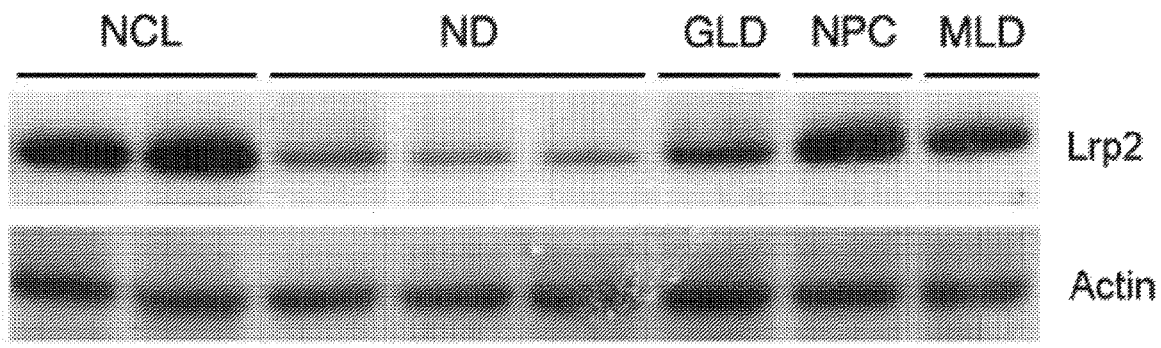
Figure 1:
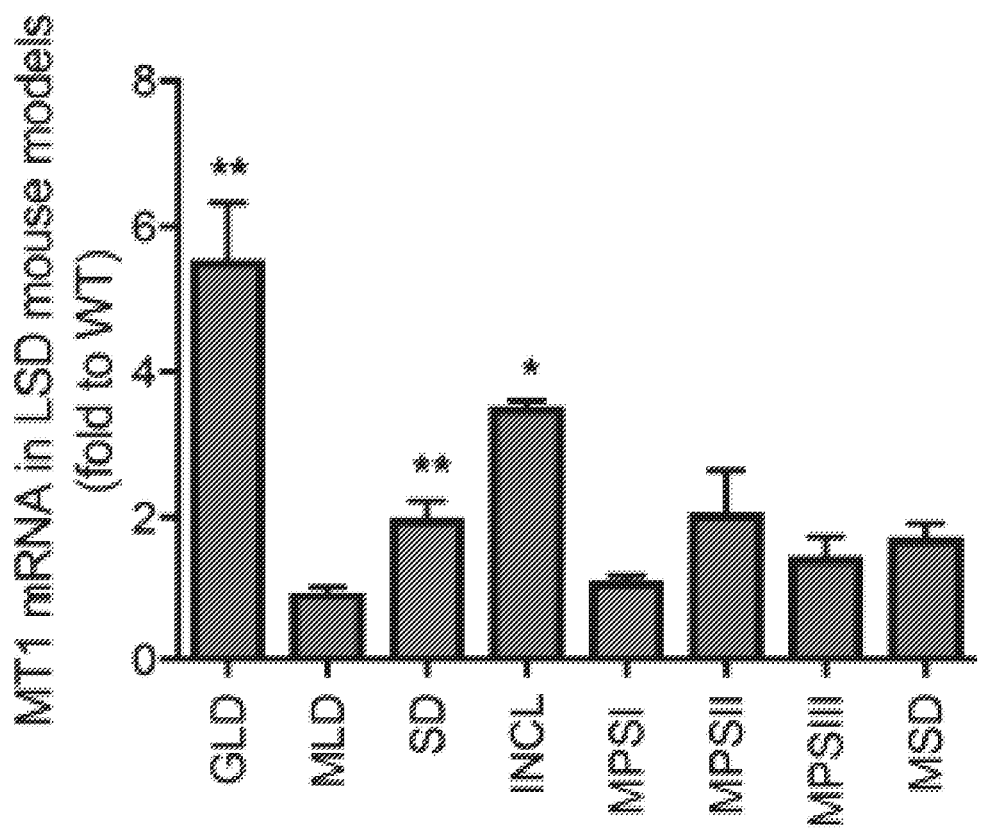

The invention features compositions and methods that are useful for the treatment and prevention of lysosomal diseases and disorders (e.g., Neuronal Ceroid Lipofuscinoses). In various embodiments, the methods involve increasing the level, expression, or activity of a metallothionein polypeptide or polynucleotide in the subject. In some embodiments, the methods involve ablating and/or reconstituting microglia.

The present invention is based at least in part on several discoveries described herein. It has been found that increasing levels of metallothionein polypeptides has a therapeutic benefit in subjects having lysosomal disease or disorder.

Lysosomal Storage Disorders (LSDs) are a broad class of inherited metabolic diseases caused by the defective activity of specific lysosomal enzymes. Central nervous system (CNS) manifestations are present in roughly 50% of LSD patients and represent an unmet medical need for patients. Disclosed herein are compositions and methods that explore the therapeutic potential of Metallothioneins (MTs), a newly identified family of proteins with reported neuroprotective roles, in murine models of two LSDs with CNS involvement.

Despite being classified and studied from more than 40 years, much knowledge is still lacking both on the pathological mechanisms responsible for the clinical manifestations and on the therapeutic approaches that could ameliorate their often fatal outcome. Current therapies include hematopoietic cell transplantation from healthy compatible donors and enzyme replacement, but for most LSDs they are not effective in treating the disease-associated neurological symptoms, due to the inability to either efficiently target the central nervous system, or to intervene on neurodegeneration in a timely manner (Escolar et al, 2005). Gene therapy using engineered autologous hematopoietic cells is an emerging promising strategy which couples the ability of transplanted-progeny cells to migrate to the recipients' brain with the possibility to reach supra-physiological levels of enzyme expression by the same tissue infiltrating cells. For some LSDs, it has already been proved to have a positive clinical outcome (Sessa M et al, 2016).

Metallothioneins (MTs) have been described as neuroprotectant molecules and possible therapeutic tools for acute and chronic brain diseases, but so far they have never been proposed for the treatment of neuronopathic LSDs. MTs are a family of metal-binding, non-enzymatic proteins that are known to exert an anti-oxidant and neuroprotective function in the diseased brain, where they are released from astrocytes and re-uptaken by astrocytes themselves and neurons through the receptor Lrp2/megalin (Chung et al, 2008). The systemic or local administration of higher than physiological levels of MTs has always been showed to be associated to a protective effect towards acute brain injury, but more recently many groups have reported a beneficial role for MT-over-expression in chronic diseases, as Parkinson's disease (Ebadi et al, 2005) Amyotrophic Lateral Sclerosis (Tokuda et al, 2014) and Alzheimer's Disease (Manso et al, 2016). We recently identified members of the Metallothionein family as highly expressed in the central nervous system of patients and mice affected by LSDs, an observation that suggests a putative role played by MTs in the pathogenesis of neural damage in these diseases (Cesani et al, 2014). Based on ours and other groups data, Metallothioneins are emerging for having a great potential as therapeutic agents for neurologic conditions.

To fully exploit this potential, the therapeutic role of MTs were investigated in alleviating neurologic damage in LSDs. To assess the effects of constitutively high levels of MTs on LSD background, a transgenic mouse over-expressing MT-1 in all tissues (strain B6.Cg-Tg(Mt1)174Bri/J, The Jackson Laboratory) were cross bred with the naturally occurring mouse model of Globoid Cell Leukodystrophy (GLD, also called Twitcher mouse) (Suzuki, 1995), being GLD a typical neuronopathic lysosomal storage disease caused by deficient activity of β-galactocerebrosidase (GALC), characterized by rapid and progressive demyelination and neuronal degeneration. The central nervous system pathology of cross-bred animals were specifically analyzed in order to gain clues on possible protective features exerted by MTs in the diseased brain. Despite a protective agent alone was not expected to cure a severe LSD as GLD, it was shown that MTs exert a beneficial effect resulting in an increased survival. Moreover, the same MT-overexpressing strategy was applied to Infantile Neuronal Ceroid Lipofuscionosis (INCL) mouse model, in order to assess MT-mediated effect in a specifically neuronal disease (Gupta et al, 2001), since neurons are the cell type mostly targeted by MT-mediated neuroprotection, and confirmed consistent beneficial effect of MT addition. In line with MT described functions, their effect is extensively related to anti-inflammatory, anti-oxidative and anti-apoptotic mechanisms.

Lysosomal Storage Diseases (LSDs)

Lysosomal Storage Disorders (LSDs) comprise more than 40 different diseases characterized by disruption of lysosomal function. Most of these conditions are characterized by unrelenting neurodegeneration. (Platt F M, Nature 2014; 510(7503)) Lysosomal dysfunction leads to accumulation of incompletely degraded substrates causing mechanical damage of the cells and/or changes in cellular homeostasis that result in apoptosis. (Futerman A H et al., Nat Rev Mol Cell Biot 2004; 5(7)) In addition, perturbation of complex cell signalling mechanisms give rise to secondary structural and biochemical changes such as inflammation that contribute to tissue damage in LSDs. Central nervous system (CNS) manifestations are present in roughly 50% of LSDs and represent an unmet medical need for patients.

Current therapies available to them comprise hematopoietic cell transplantation from healthy compatible donors, enzyme replacement therapy, and substrate reduction strategies. These approaches are generally not or only partially effective in treating the LSD neurological symptoms due to the inability to efficiently target the CNS, intervene on neural damage in a timely manner or target the complex LSD brain pathology, particularly in symptomatic patients. (Musolino P L et al., Neuropediatrics 2014; 45(3)) Innovative therapeutic strategies have been or are currently being tested in the context of early phase clinical trials. These novel approaches aim at effective enzyme delivery to the LSD CNS and comprise brain directed enzyme replacement strategies (i.e. ClinicalTrials.gov #NCT02055118), in vivo gene therapy by direct intra-parenchymal/intra-thecal gene transfer (i.e. ClinicalTrials.gov #NCT01801709 and NCT02725580), or ex vivo gene therapy, i.e. based on hematopoietic stem cells (i.e. ClinicalTrials.gov #NCT01560182). Interestingly, promising results were observed in patients treated in pre-symptomatic stage by the latter strategy. (Biffi A., Hum Mol Genet 2016; 25(R1); Sessa M. et al., Lancet 2016; 388(10043)) However, despite these early promising findings, most LSD patients with CNS involvement lack a curative treatment.

Lysosomal storage diseases include, without limitation, Neuronal Ceroid Lipofuscinoses (NCL), GM1 and GM2 Gangliosidosis, Alpha-mannosidosis, Globoid Cell Leukodystrophy (GLD), Neuronal Ceroid Lipofuscinosis (NCL), Metachromatic Leukodystrophy (MLD), Mucopolysaccharidoses disorders (MPSs), Multiple sulfatase deficiency (MSD), and Niemann-Pick Disease. Approximately 50% of LSDs have involvement of the CNS, as in the case of the examples listed above. A non-limiting list of exemplary SDs and their associated defective protein is provided at Table 1.

TABLE 1

Lysosomal Storage Disorders (LSDs) and their associated defective protein

| Lysosomal Storage Disorder | Defective Protein |
| --- | --- |
| Pompe disease | Acid α-glucosidase |
| Gaucher disease | Acid β-glucosidase or glucocerebrosidase |
| $G_{M1}$-gangliosidosis | Acid β-galactosidase |
| Tay-Sachs disease | β-Hexosaminidase A |
| Sandhoff disease | β-Hexosaminidase B |
| Niemann-Pick disease | Acid sphingomyelinase |
| Krabbe disease | Galactocerebrosidase |
| Farber disease | Acid ceramidase |
| Metachromatic leukodystrophy | Arylsulfatase A |
| Hurler-Scheie disease | α-L-Iduronidase |
| Hunter disease | Iduronate-2-sulfatase |
| Sanfilippo disease A | Heparan N-sulfatase |
| Sanfilippo disease B | A-N-Acetylglucosaminidase |
| Sanfilippo disease C | Acetyl CoA; α-glucosaminide N-acetyltransferase |
| Sanfilippo disease D | N-acetylglucosamine-6-sulfate sulfatase |
| Morquio disease A | N-acetylgalactosamine-6-sulfate sulfatase |
| Morquio disease B | Acid β-galactosidase |
| Maroteaux-Lamy disease | Arylsulfatase B |
| Sly disease | B-Glucoronidase |
| Alpha-mannosidosis | Acid α-mannosidase |
| Beta-mannosidosis | Acid β-mannosidase |
| Fucosidosis Acid | α-L-fucosidase |
| Sialidosis | Sialidase |
| Schindler-Kanzaki disease | α-N-acetylgalactosaminidase |

In one aspect, disclosed herein is information of some LSDs of particular relevance for the use of HSC-transplant protocols as described in some aspects of the present invention.

Neuronal Ceroid Lipofuscinoses (NCLs)

Neuronal Ceroid Lipofuscinoses are a class of inherited storage disorder that result in progressive neurological degeneration. Some variants, such as the late infantile NCL (LINCL), are caused by deficiency of a lysosomal enzyme. LINCL is caused by mutations in the CLN2 gene that result in the deficiency of TPP-I, a lysosomal enzyme that is responsible for degrading membrane proteins. Neurons are particularly sensitive to the lysosomal accumulation of this storage material, and individuals with LINCL have extensive, progressive neurodegeneration in all parts of the brain, resulting in a vegetative state and death by the age of 8-12 years.

Metachromatic Leukodystrophy (MLD)

Metachromatic Leukodystrophy (MLD), a demyelinating LSD due to mutations in the Arylsulfatase A (ARSA) gene is a prototypical example of LSD with progressive accumulation of un-degraded substrates in the nervous system and secondary neuroinflammation and degeneration. The genetic transmission of MLD is autosomal recessive and its overall incidence is estimated to be 1:40,000-1:100,000.

Clinical manifestations, consisting of severe and unrelenting motor and cognitive impairment, and disease progression are more severe in the early onset clinical variants, leading to death usually within the first decade of life. A correlation between the phenotype of MLD patients and the type of ARSA mutation they bear has been demonstrated. HSC gene therapy employing lentiviral vectors for autologous HSC transduction and exposure to systemic busulfan conditioning was shown to be effective in preventing or relenting disease manifestations in children affected by the most severe MLD variant and treated before symptom onset.

Globoid Cell Leukodystrophy (GLD)

Globoid Cell Leukodystrophy (GLD), also known as Krabbe disease, is an autosomal recessive LSD caused by deficiency of the lysosomal enzyme Galactocerebrosidase (GALC) which catalyzes the catabolism of Galactosylceramide (GalCer), an important myelin constituent. GLD occurs in about 1 in 100,000 births. It typically occurs among infants and takes rapidly a fatal course, but rare late-onset forms also exist. The devastating neurodegenerative disorder is due to alterations in glycosphingolipid catabolism caused by GALC deficiency: the resulting accumulation of incompletely metabolized GalCer leads to progressive white matter disease which affects both the CNS and the Peripheral Nervous System (PNS). Galactosylsphingosine (or psycosine) is also a substrate of GALC and it is considered to play a critical role in the pathogenesis. GLD children can be treated when pre-symptomatic and below the age of 4-month-old by HCT from healthy compatible donors that delays disease onset and attenuates manifestations[20]. HSC gene therapy was also proven to be potentially effective in GLD preclinical models[21].

Mucopolysaccharidoses (MPSs)

Mucopolysaccharidoses (MPS) are a group of LSDs caused by the absence or malfunctioning of lysosomal enzymes needed to break down glycosaminoglycans. MPS I is divided into three subtypes based on severity of symptoms. All three types result from an absence of, or insufficient levels of, the enzyme alpha-L-iduronidase. MPS I H (also called Hurler syndrome or α-L-iduronidase deficiency), is the most severe of the MPS I subtypes while MPS I S, Scheie syndrome, is the mildest form of MPS I. MPS I H-S, Hurler-Scheie syndrome, is less severe than Hurler syndrome alone. MPS II, Hunter syndrome or iduronate sulfatase deficiency, is caused by lack of the enzyme iduronate sulfatase. MPS III, Sanfilippo syndrome, is marked by severe neurological symptoms. There are four distinct types of Sanfilippo syndrome, each caused by alteration of a different enzyme needed to completely break down the heparan sulfate sugar chain. Sanfilippo A is the most severe of the MPS III disorders and is caused by the missing or altered enzyme heparan N-sulfatase. Children with Sanfilippo A have the shortest survival rate among those with the MPS III disorders. Sanfilippo B is caused by the missing or deficient enzyme alpha-N acetylglucosaminidase. Sanfilippo C results from the missing or altered enzyme acetyl-CoAlpha-glucosaminide acetyltransferase. Sanfilippo D is caused by the missing or deficient enzyme N-acetylglucosamine 6-sulfatase. MPS IV, Morquio syndrome, results from the missing or deficient enzymes N-acetylgalactosamine 6-sulfatase (Type A) or beta-galactosidase (Type B) needed to break down the keratan sulfate sugar chain. MPS VI, Maroteaux-Lamy syndrome, shares many of the physical symptoms found in Hurler syndrome and is caused by the deficient enzyme N-acetylgalactosamine 4-sulfatase. MPS VII, Sly syndrome, one of the least common forms of the mucopolysaccharidoses, is caused by deficiency of the enzyme beta-glucuronidase. Some MPS patients were shown to benefit from HCT from healthy compatible donors, whereas for some to MPSs HSC GT strategies are being optimized[22].

Neurodegenerative Manifestations in LSDs

Neurodegenerative diseases are characterized by the progressive loss of the structure and/or function of neurons and/or neuronal cell death. Inflammation has been implicated for a role in several neurodegenerative diseases. Progressive loss of motor and sensory neurons and the ability of the mind to refer sensory information to an external object is affected in different kinds of neurodegenerative diseases. A health care professional may diagnose a subject as having a neurodegenerative disease by the assessment of one or more symptoms of a neurodegenerative disease in the subject. Non-limiting symptoms of a neurodegenerative disease in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disease. A health care professional may diagnose a subject as having a neurodegenerative disease upon presentation of a subject to a health care facility (e.g., a clinic or a hospital). In some instances, a health care professional may diagnose a subject as having a neurodegenerative disease while the subject is admitted in an assisted care facility. Typically, a physician diagnoses a neurodegenerative disease in a subject after the presentation of one or more symptoms.

Metallothioneins

Metallothioneins (MTs) are a family of metal-binding, non-enzymatic proteins known to exert an anti-oxidant and neuroprotective function in the diseased brain in several different pathological conditions. (Ebadi M H et al., Brain Res Mol Brain Res 2005; 134(1); Tokuda E. et al., Hum Mol Genet 2014; 23(5); Manso Y. et al., J Alzheimers Dis 2016; 51(1)) MTs are released from astrocytes and re-uptaken by astrocytes themselves and neurons through the receptor Lrp2/megalin. (Chung, R S. et al., J Neurochem 2008; 104(1)) Recently, it was shown that members of the MT family are highly expressed in the CNS of patients and mice affected by LSDs, an observation that suggests a putative role for MTs in the LSD neurodegenerative process. (Cesani M. et al., Ann Neurol 2014; 75(1): 127-137) Mechanistically, it was demonstrated that MT expression in LSDs is a response to the oxidative and inflammatory processes that are associated with inhibition of autophagy caused by lysosomal dysfunction. (Cesani M. et al., Ann Neurol 2014; 75(1); Baird S K. et al., Biochem J 2006; 394(Pt 1)) Up-regulation of MTs could represent an endogenous mechanism to counterbalance the LSD-associated inflammation and oxidative stress, and ultimately exert some neuroprotective effects. (Filippon L. et al. Mol Genet Metab 2011; 103(2)) Based on these assumption and data, it ws investigated whether delivery of MTs could exert a therapeutic effect and alleviate neural damage in LSDs. Two MT-transgenic disease models (of Neuronal Ceroid Lipofuscinosis—NCL, also known as Batten disease, and Globoid Cell Leukodystrophy—GLD, also known as Krabbe disease) were generated and analysed, characterized by the presence of constitutively high levels of MTs in all body tissues, including the CNS. Despite a protective agent alone was not expected to cure severe inborn errors of metabolism as the ones here studied, MTs exerted a beneficial effect on diseased mice phenotype. This beneficial effect, was also achieved when MT transcripts were delivered to mutant LSD mice by systemic administration of a MT-encoding AAV-PHP.B vector (Deverman B E. et al., Nat Biotechnol 2016; 34(2)), and was extensively related to anti-inflammatory, anti-oxidative and anti-apoptotic effects exerted by the MTs in the LSD CNS.

Thus, in one aspect, the compostions and methods disclosed herein, as supported by the data, indicate that exogenously delivered MTs could exert a therapeutic role in LSDs severely affecting the CNS by modulating disease-related mechanisms of neural damage.

Methods of Treatment

The present invention provides methods of treating a lysosomal storage disease or disorder in a subject involving increasing the level, expression, or activity of a metallothionein polyepeptide or polynucleotide in the subject. Metallothioneins (MTs) are a family of small (~6-7 kDa), heat-resistant proteins containing 25-30% cysteine residues that are evolutionarily highly conserved in a broad range of species from yeast to mammals. MTs are up-regulated by glucocorticoids, oxidative stress and a variety of heavy metals, such as copper, cadmium, mercury and zinc (Andrews (2000) Biochem. Pharmacol. 59, 95-104). Isoforms range from MT-1 to MT-4 and have slightly different amino acid composition. MTs bind metals and protect against their toxicity, as was first demonstrated in aquatic species, such as fish, arthropods and molluscs from contaminated waters. Apart from binding heavy metals, MTs are considered to act as antioxidants, although by undetermined mechanisms. Thus MTs have been found to protect against apoptosis/necrosis induced by oxidative stress, etoposide, cisplatin, doxorubicin and X-irradiation (Cai et al. (2004) Toxicol. Lett. 146, 217-226; Chimienti et al. (2001) Free Radicals Biol. Med. 31, 1179-1 190; Wang et al. (2001) J. Pharmacol. Exp. Ther. 298, 461-468).

The MT transcript and protein described herein may be selected from, for example, metallothionein-1A (MT1A), metallothionein-1B (MT1B), metallothionein-1E (MT1E), metallothionein-1F (MT1F), metallothionein-1G (MT1G), metallothionein-1H (MT1H), metallothionein-lI pseudogene (MT1Ip or MTE), metallothionein-1L (LT1L or MT1R), metallothionem-1M (MT1M or MT1K), metallothionein-1X (MT1X), metallothionein-2 (MT2), metallothionein-2A (MT2A), metallothionein-3 (MT3) or metallothionein-4 (MT4).

The NCBI protein accession numbers of the main members of the family are: NP_005937 (MT1A); NP_005938 (MT1B); NP_783316 (MT1E); NP_005940 (MT1F); NP_005941 (MT1G); NP_005942 (MT1H); NP_789846 (MT1M); NP_005943 (MT1X); NP_005944 (MT2); NP_005945 (MT3); and NP_116324 (MT4). Further NCBI accession numbers for MT1A, MT1E, MT2A and MTE-MT1IP include: NM_005946, NM_075617, NM_005953 and NR_0303669, respectively.

The present invention also provides methods of treating disease and/or disorders or symptoms thereof which comprise administering a therapeutically effective amount of a pharmaceutical composition comprising HSCs described herein to a subject (e.g., a mammal such as a human). Thus, one embodiment is a method of treating a subject suffering from or susceptible to a disease or disorder or symptom thereof. The method includes the step of administering to the mammal a therapeutic amount of a cell herein sufficient to treat the disease or disorder or symptom thereof, under conditions such that the disease or disorder is treated.

The methods herein include administering to the subject (including a subject identified as in need of such treatment) an effective amount of a cell described herein, or a composition described herein to produce such effect. Identifying a subject in need of such treatment can be in the judgment of a subject or a health care professional and can be subjective (e.g. opinion) or objective (e.g. measurable by a test or diagnostic method).

Engraftment of transplanted cells provides the expression or activity of a polypeptide or other therapeutic agent. For example, a deficiency in or loss of function of a lysosomal enzyme results in a lysosomal storage disorder. Transplanted hematopoietic cells that express the therapeutic protein (e.g., an enzyme) either endogenously or via recombinant methods engraft and differentiate into microglia, thereby remedying the deficiency in the enzyme. Additionally, transplanted cells may serve as a vehicle for therapeutic polypeptides (e.g., one or more metallothionein polypeptides).

In certain embodiments, engraftment is enhanced by ablating existing microglia nd/or their progenitors (e.g., with alkylating agents).

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method). Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

Antibodies

As reported herein, antibodies that specifically bind a marker (e.g., of a microglial cell or precursor thereof) are useful in the methods of the invention, including therapeutic methods. In particular embodiments, the invention provides methods of ablating microglia involving contacting microglia with a nanoparticle having a capture molecule that specifically binds a marker of a microglial cell and containing a cytotoxic agent (e.g., an alkylating agent).

Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. As used herein, the term "antibody" means not only intact antibody molecules, but also fragments of antibody molecules that retain immunogen-binding ability. Such fragments are also well known in the art and are regularly employed both in vitro and in vivo. Examples of antibody fragments include, but are not limited to, Fab, Fab', F(ab')2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments.

The antibodies in the present invention may exist in a variety of forms including, for example, polyclonal antibodies, monoclonal antibodies, Fv, Fab and F(ab')2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). For example, F(ab')$_2$, and Fab fragments that lack the Fc fragment of an intact antibody, clear more rapidly from the circulation, and may have less non-specific tissue binding than an intact antibody (Wahl et al., J. Nucl. Med. 24:316-325 (1983). Thus, the antibodies of the invention comprise, without limitation, whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062,1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and using unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In various embodiments, an antibody is monoclonal. Alternatively, the antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Methods of preparing antibodies are well known to those of ordinary skill in the science of immunology. Antibodies can be made by any of the methods known in the art utilizing a soluble polypeptide, or immunogenic fragment thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding polypeptides or immunogenic fragments thereof, can be provided to the host in a delivery vehicle that is taken up by immune cells of the host. The cells will in turn express the polypeptide thereby generating an immunogenic response in the host. Alternatively, nucleic acid sequences encoding human polypeptides or immunogenic fragments thereof, can be expressed in cells in vitro, followed by isolation of the polypeptide and administration of the polypeptide to a suitable host in which antibodies are raised.

Alternatively, antibodies may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naïve histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Hematopoietic Cell Transplantation (HCT)

Recent pre-clinical and clinical evidences indicate that hematopoietic stem and progenitor cells (HSPCs) and/or their progeny can serve as vehicles for therapeutic molecule delivery across the blood brain barrier by contributing to the turnover of myeloid cell populations in the brain. However, the differentiation and functional characteristics of the cells reconstituted after transplantation are still to be determined, and in particular whether bona fide microglia could be reconstituted by the donor cell progeny post-transplant to be assessed. In the last three decades, Hematopoietic Cell Transplantation (HCT) and Hematopoietic Stem Cell (HSC)-based gene therapy have been applied with some benefit to patients affected by non-hematological and non-oncological diseases affecting the nervous system, such as lysosomal storage diseases (LSDs) and neurodegenerative diseases. These early clinical evidences, along with preclinical supporting data, suggest that hematopoietic stem and progenitor cells (HSPCs) and/or their progeny could serve as vehicles for therapeutic molecule delivery across the blood brain barrier (BBB). Indeed, HSPCs and/or their progeny could contribute to the turnover of myeloid cell populations in the brain, possibly including microglia, whose crucial role in the progression and outcomes of these disorders has been extensively described. Importantly, once integrated into the affected tissue, cells derived from the transplant were proven to favorably affect the local environment, i.e. by releasing therapeutic molecules in the brain of transplanted mice or patients. This concept was demonstrated in patients affected by the demyelinating LSD metachromatic leukodystrophy treated by HSC gene therapy. Normal or above-normal activity of arylsulfatase A enzyme, defective in the patients and whose expression was induced by lentiviral vectors (LVs) integrated into the patients HSCs and their progeny, was measured in the treated children' cerebrospinal fluid (CSF) long after the treatment. Notably, the enzyme is unable to efficiently cross per se the BBB. These findings, which were associated to marked clinical benefit in the patients treated in pre-symptomatic stage, formally prove that the patients' brain were seeded by gene-corrected HSPC progeny cells.

Members of the Metallothionein family were recently identified as highly expressed in the central nervous system of patients and mice affected by LSDs, an observation that suggests a putative role played by MTs in the pathogenesis of neural damage in these diseases (Cesani et al, 2014). As disclosed herein, Metallothioneins are emerging for having a great potential as therapeutic agents for neurologic conditions.

Recombinant Polypeptide Expression

In order to express the polypeptides of the invention, DNA molecules obtained by any of the methods described herein or those that are known in the art, can be inserted into appropriate expression vectors by techniques well known in the art. For example, a double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a polypeptide, or fragment thereof, operatively linked to regulatory sequences, e.g., promoter sequences, terminator sequences, and the like, as defined herein. Recombinant vectors which allow for expression of the genes or nucleic acids included in them are referred to as "expression vectors."

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Methods for Evaluating Therapeutic Efficacy

In one approach, the efficacy of the treatment is evaluated by measuring, for example, the biological function of the treated organ (e.g., neuronal function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is neuronal tissue and, preferably, the organ is brain.

In another approach, the therapeutic efficacy of the methods of the invention is assayed by measuring an increase in cell number in the treated tissue or organ as compared to a corresponding control tissue or organ (e.g., a tissue or organ that did not receive treatment). Preferably, cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif.). For example, assays for cell proliferation may involve the measurement of DNA synthesis during cell replication. In one embodiment, DNA synthesis is detected using labeled DNA precursors, such as $[^{3H}]$-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302 (5650):1581-4, 2003; Gu et al., Science 302 (5644):445-9, 2003).

Kits

The invention provides kits for the treatment or prevention of a lysosomal storage disease or disorder (e.g., Neuronal Ceroid Lipofuscinoses) by increasing the level, expression, or activity of one or more metallothionein polypeptides in a subject. In one embodiment, the kit includes a composition containing an isolated hematopoietic stem cell expressing one or more metallothionein polypeptides. In another embodiment, the kit includes a nanoparticle for ablative conditioning of endogenous microglial cells.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a neurological disease or disorder of the central nervous system. The instructions will generally include information about the use of the composition for the treatment or prevention of the disease or disorder. In other embodiments, the instructions include at least one of the following: description of the therapeutic agent; dosage schedule and administration for treatment or prevention of a neurological disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Disease Model Selection for Preclinical Testing of Metallothioneins as Therapeutic Agents in LSDs Based on our previous findings (Cesani M. et al., Ann Neurol 2014; 75(1)), LSDs with both white and grey matter involvement could be considered as good candidates for testing MTs as possible neuroprotective agents for LSDs with CNS involvement. To identify relevant target diseases for our strategies human brain samples were examined from LSD patients. Samples from patients affected by four different LSDs were accessed, two characterized by primary white matter damage namely MLD, caused by mutations in the Arylsulfatase A gene (OMIM #250100), and GLD, caused by mutations in the galactocerebrosidase gene (OMIM #245200); and two characterized by grey matter involvement, namely NPC type C (OMIM #257220) and NCL. MT immunoreactivity was documented in all the tested LSD brains (FIG. 1A). MT signal was mostly detected in the grey matter of all the LSD brain samples, including the MLD and GLD ones. Astrocytes acted as primary MT-over-expressing cells in every tested sample. In the MLD samples MT signal was also identified in histiocytic cells. Interestingly, MT immunoreactivity was identified in neurons only in the NCL brain samples. Without being bound by theory, this indicates a possible mechanism of re-uptake on going in this specific disease. The expression of Lrp2 was then measured, the MT receptor known to be responsible for MT uptake by neurons and for their neuroprotective activity, on the same samples. Both RNA and protein analysis demonstrated Lrp2 up-regulation in samples from the two LSDs with grey matter involvement (FIG. 1B and FIG. 1C) and particularly in INCL brains. High MT transcript levels were also measured in brain tissues retrieved from INCL-affected mice (characterized by palmitoyl protein thioesterase-1 (PPT1) deficiency) (FIG. 1D). Based on these findings we thus selected INCL as disease platform of potential value to test MT neuroprotective role in LSDs, and in particular we employed the INCL animal model. Moreover, to understand if MTs could be similarly beneficial in other LSDs also or primarily affecting the white matter, based on the immunoreactivity human data and the murine MT transcript levels, for further experiments GLD (due to Galactocerebrosidase—GALC deficiency) were selected, in which MTs were shown to vary along with disease progression and upon therapeutic treatment (Cesani M. et al., Ann Neurol 2014; 75(1)).

Figure 2:
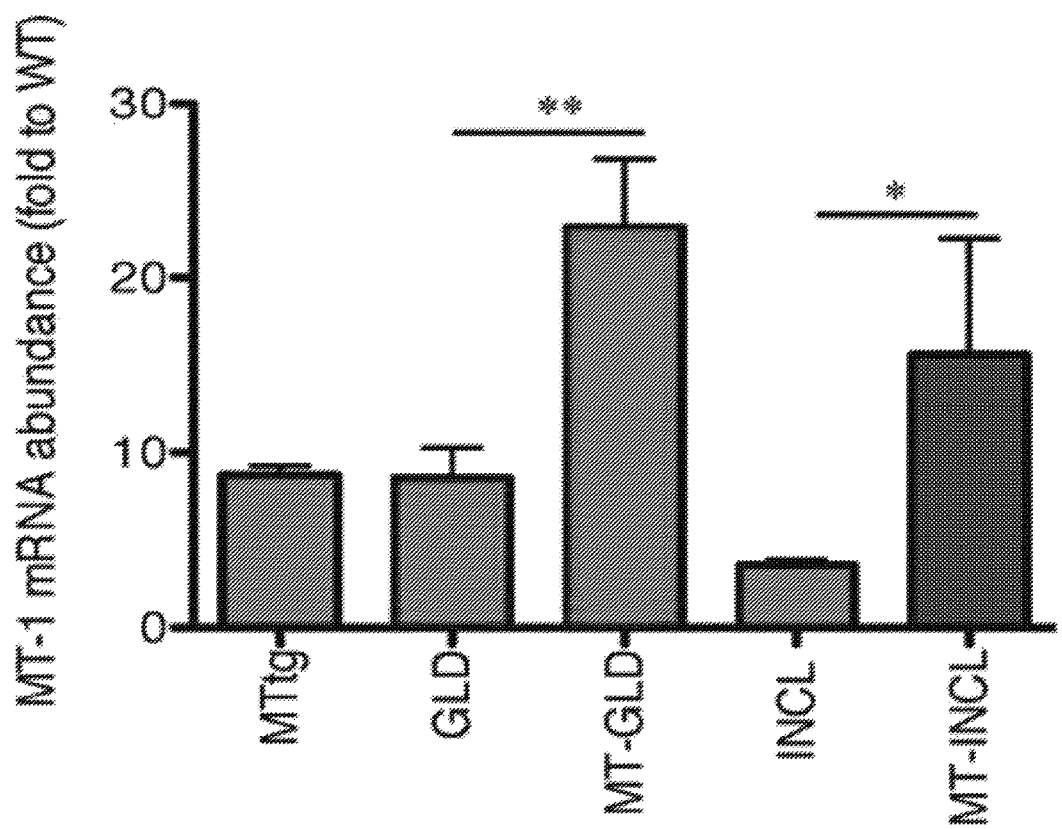
FIG. 2A, FIG. 2B, FIG. 2C, FIG. 2D, FIG. 2E, FIG. 2F, FIG. 2G, and FIG. 2H show phenotypic effects of MTs in the GLD and INCL animal models.
Figure 2:
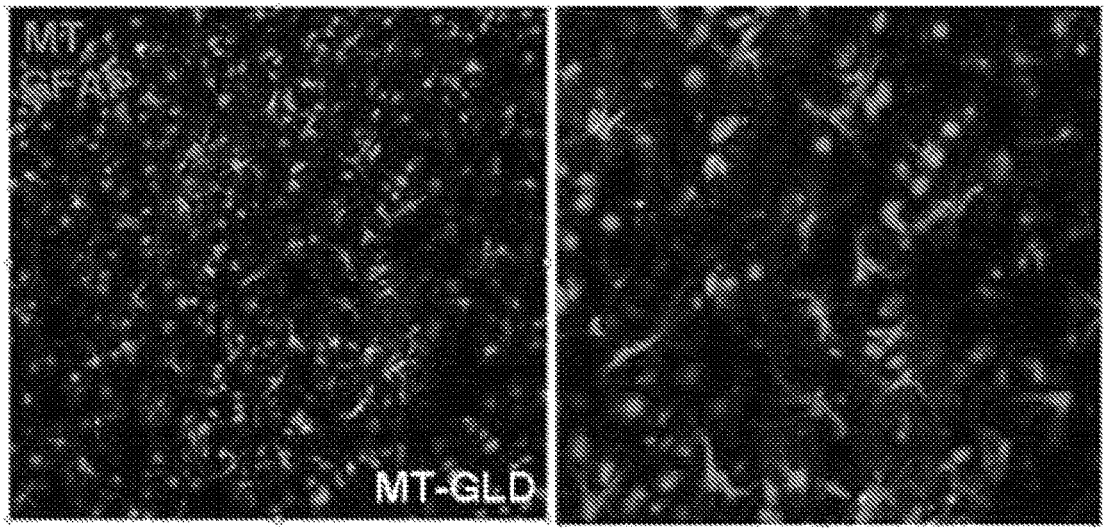
Figure 2:
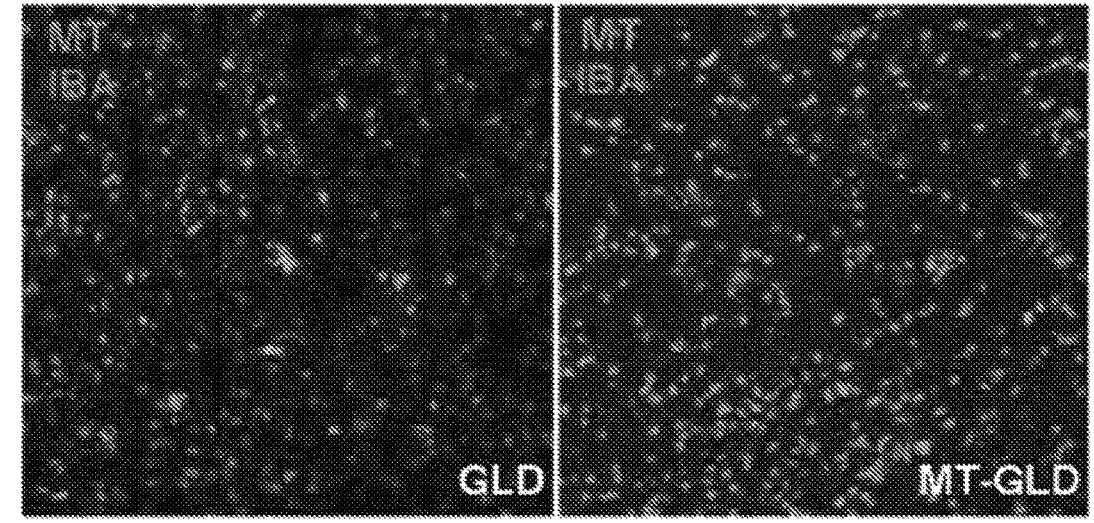
Figure 2:
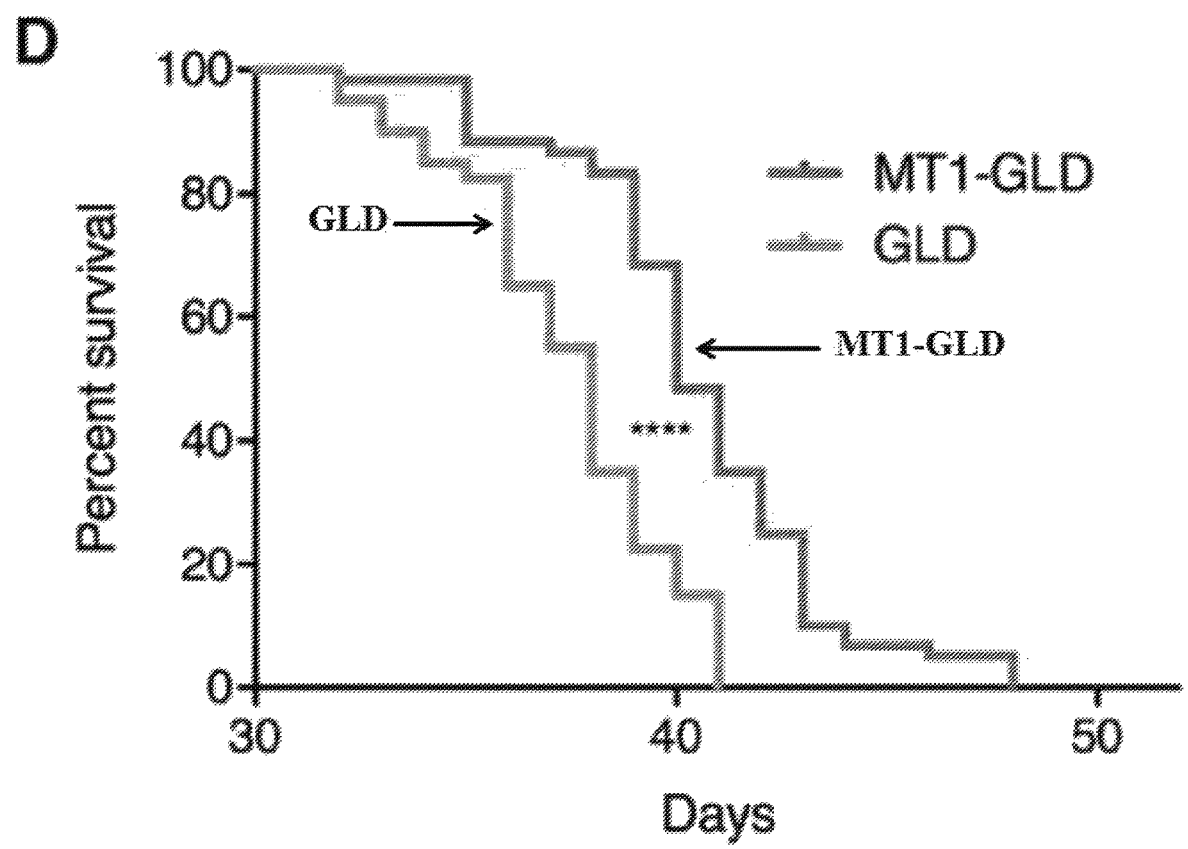
Figure 2:
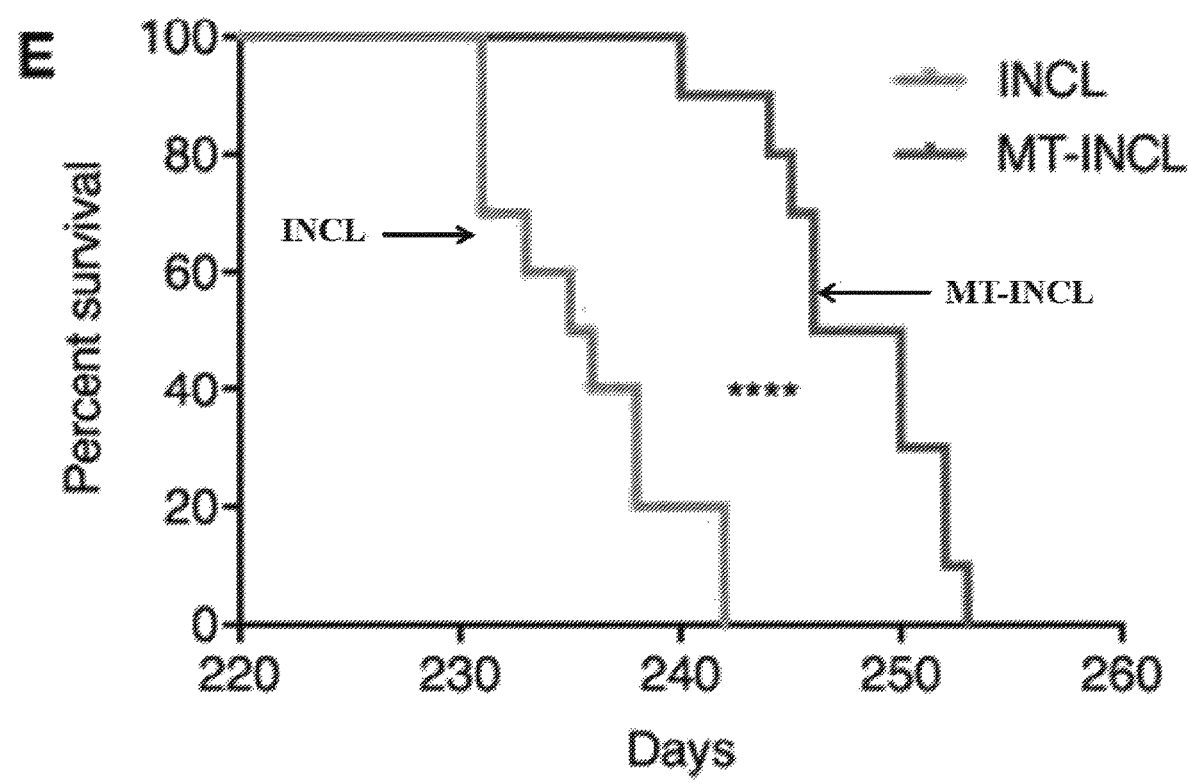
Figure 2:
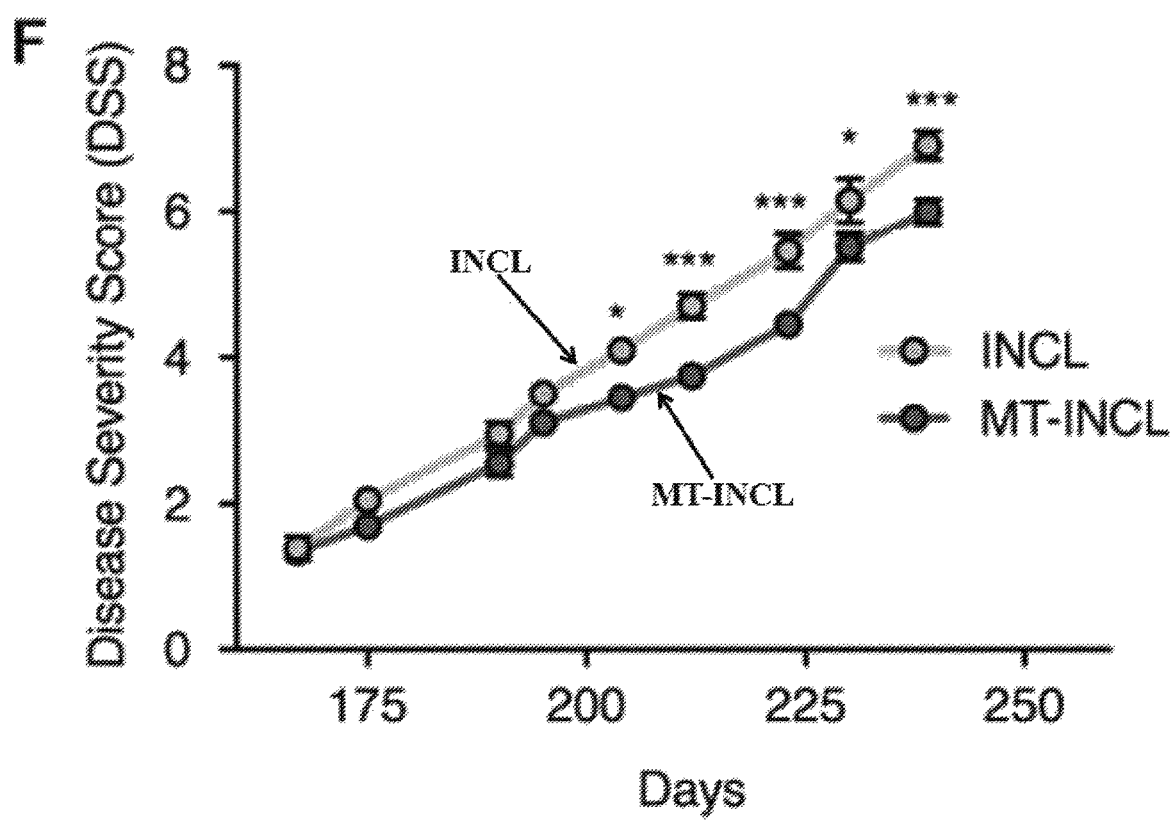
Figure 2:
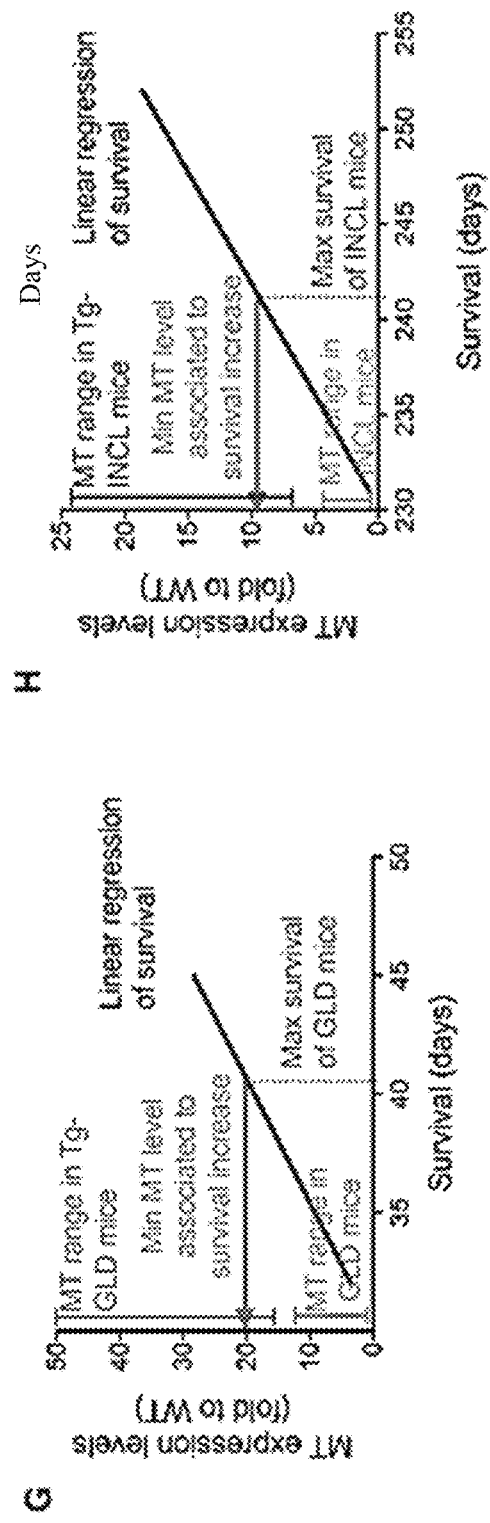

Example 2: Phenotypic Effects of Metallothioneins in the GLD and INCL Animal Models To assess whether exogenous MT delivery to the CNS of INCL and GLD mice could favourably affect their disease phenotype, a MT-1 over-expressing transgenic mouse (MTtg) bearing multiple copies of the MT-1 gene (Palmiter R D. et al., Mol Cell Biol 1993; 13(9)) and expressing high MT-1 transcript levels both in the brain and peripheral tissues was taken advantage of (Comes G. et al., Int J Mol Sci 2017; 18(2); and data not shown). MTtg mice were cross-bred with GLD and INCL heterozygous animals to generate GLD and INCL homozygous defective mice with constitutive high MT-1 levels in their tissues (MT-GLD and MT-INCL, respectively). High levels of MT-1 expression (FIG. 2A) were measured in the brain of these mice. Interestingly, in both settings the MT-1 expression levels resulted from the contribution of both the MT transgenic background and the disease setting per se. MT signal in the disease transgenic brains mostly co-localized with astrocytes, in line with the preferentially described expression pattern in the brain (Vela J M et al., Brain Res 1997; 767(2)) (FIG. 2B), and only a fraction of the microglia cells showed MT immunostaining (FIG. 2C). Interestingly, MT over-expression determined a therapeutic benefit in both the examined models. Indeed, MT-GLD transgenic mice showed a significantly increased survival as compared to not-transgenic affected GLD controls (approximately 10%, with a median survival of 40.5 days for MT-GLD and 37.5 days for GLD), which have a very short life expectancy and an extremely severe phenotype (FIG. 2D). Similarly, MT-INCL mice showed an increased survival compared to not-transgenic, affected INCL mice (FIG. 2E) (approximately 5%, with a median survival of 248 days in MT-INCL a nd of to 235.5 days in INCL), as well as an amelioration of their phenotype (FIG. 2F), as documented by a disease specific severity score. To identify the minimum increase in MT transcript levels in the brain associated to a survival increase in the two tested animal models, MT expression levels were plotted against survival data collected in both LSD and MT-LSD mice (FIGS. 2G and 2H). Analysis of these data showed that MT levels equal or superior to 10-20 folds the wild type MT expression levels are associated with increased survival of MT-INCL and MT-GLD mice versus the corresponding INCL and GLD animals, respectively (FIGS. 2G and 2H). Since both disease models in their original background are characterized by disease-associated high MT expression in the brain, this threshold for benefit translates into the need to increase the MT expression level of 1.5 to 2 folds on top of basal disease levels for GLD and INCL, respectively (FIGS. 2G and 2H).

Figure 3:
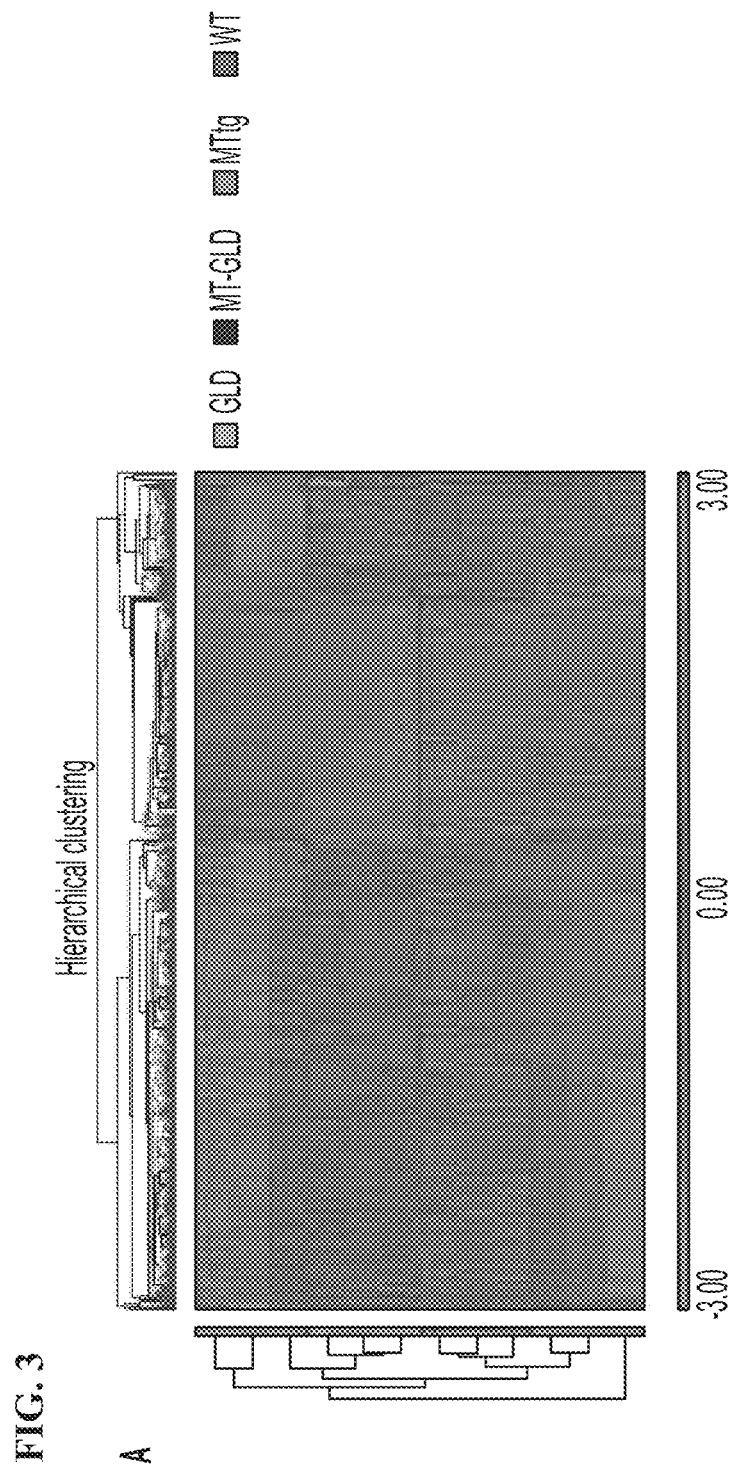
FIG. 3A, FIG. 3B, FIG. 3C, FIG. 3D, FIG. 3E, FIG. 3F, and FIG. 3G show modulation of anti-inflammatory, anti-apoptotic and anti-oxidative stress genes in MT-GLD and MT-INCL mice.
Figure 3:
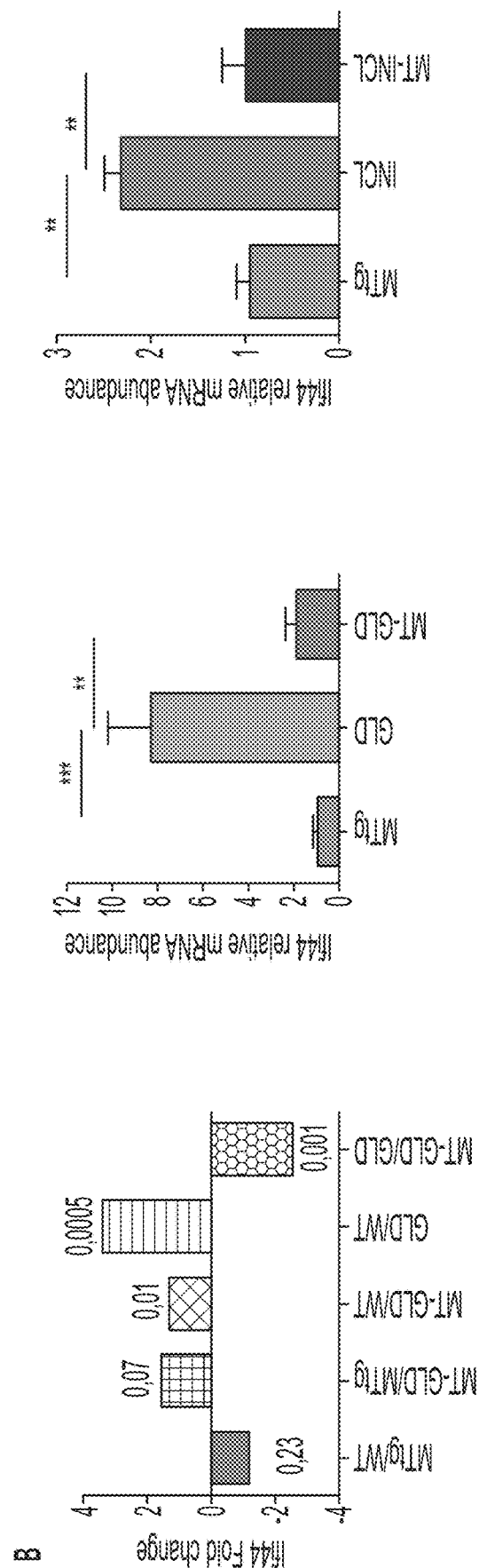
Figure 3:
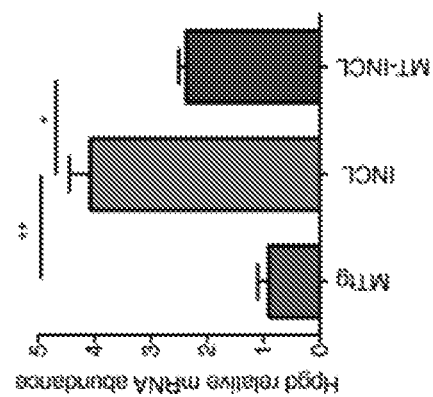
Figure 3:
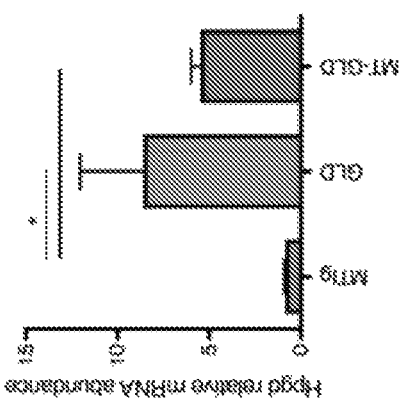
Figure 3:
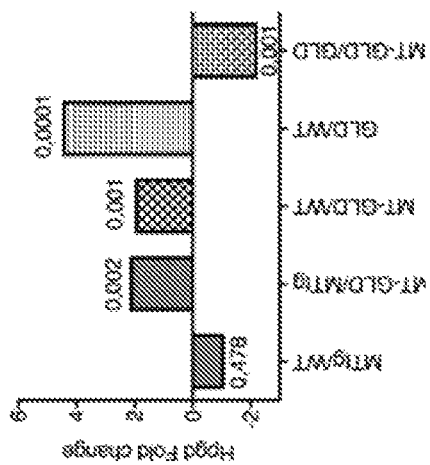
Figure 3:
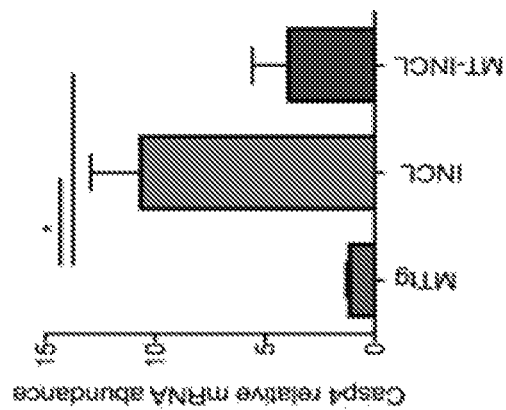
Figure 3:
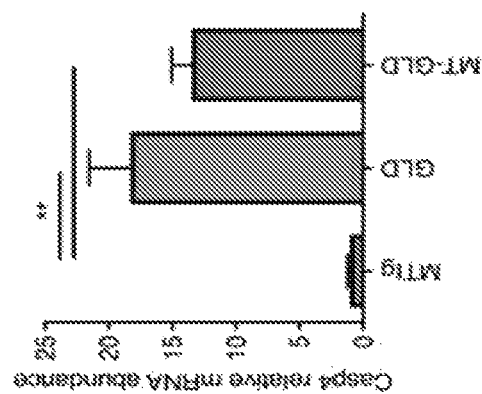
Figure 3:
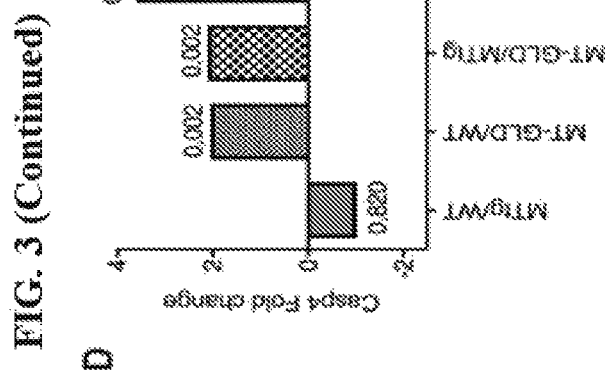
Figure 3:
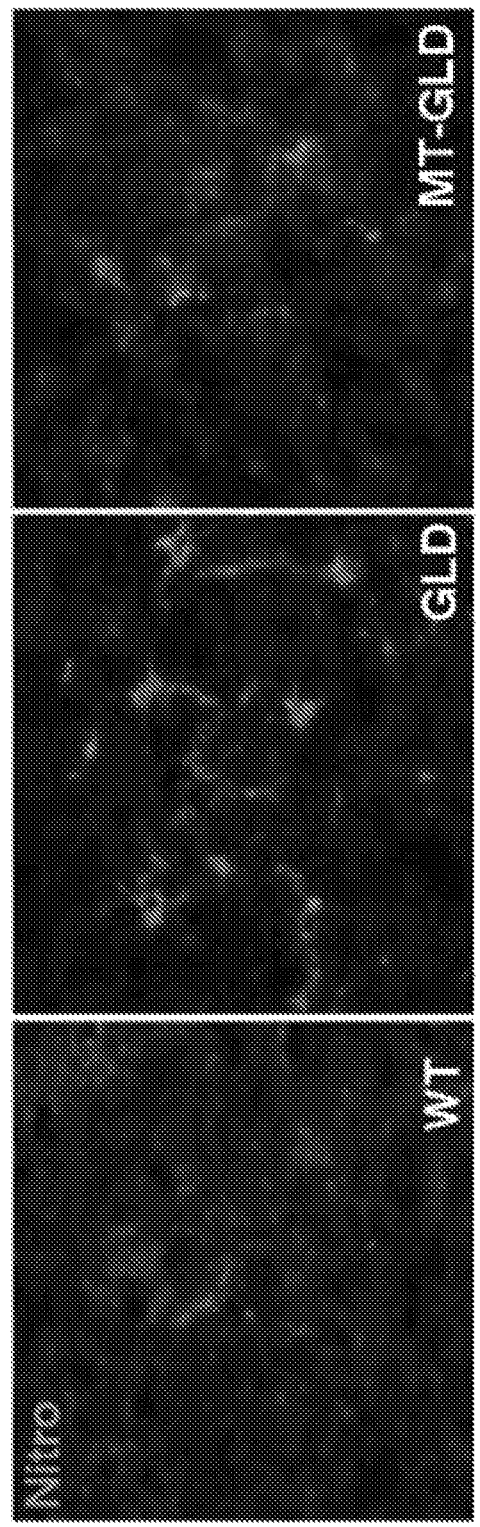
Figure 3:
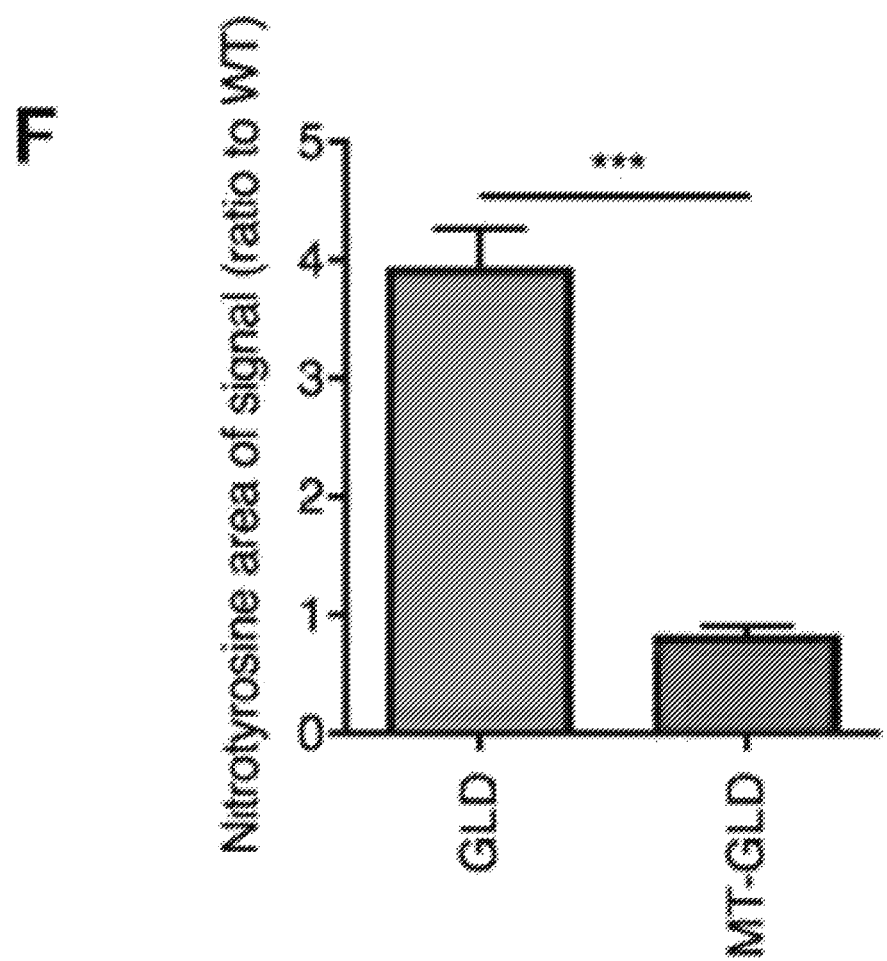
Figure 3:
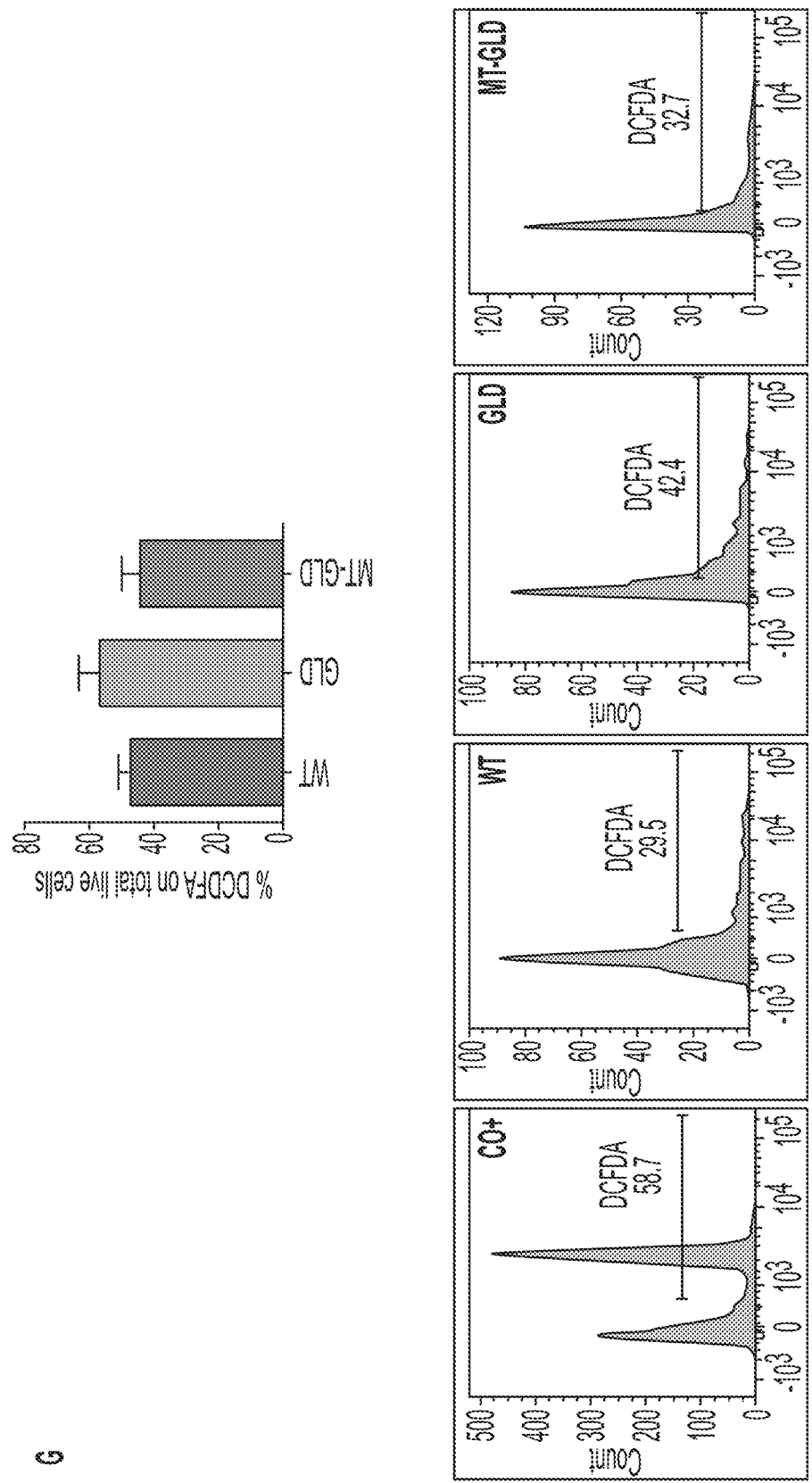

Example 3: Modulation of Anti-Inflammatory, Anti-Apoptotic and Anti-Oxidative Stress Genes in MT-GLD and MT-INCL Mice To identify the aspects of the complex neurodegenerative LSD process that were modulated by MT-over-expression, a whole transcriptome analysis was ran on brain extracts from wild type (WT), MTtg, GLD and MT-GLD mice (n=3 per group). Lists of differentially expressed genes were generated setting a cutoff fold change of 2, considering only genes with an associated RefSeq ID, and generating a hierarchical clustering aimed at identifying intra-condition expression profile. This distribution was reflecting a differential gene expression in the four tested groups with a major difference in MT-GLD as compared to the others. Many down-regulated genes were identified in MT-GLD mice as compared to the GLD group (FIG. 3A). Few genes were over-expressed in MTtg samples as compared to WT and they were mostly non-coding transcripts included in the Affymetrix platform. The genes down-regulated in the MT-GLD model versus GLD identified functions related to neurotransmitter receptor activity, ion channel activity (voltage-gated potassium and calcium channels), transport channels, and others, indicating a possible new mechanism of MT action regulating brain network stability. Other genes involved in inflammatory and apoptotic pathways were significantly down-regulated in MT-GLD versus GLD mice in the transcriptome array (FIG. 3B, FIG. 3C, FIG. 3D). These genes were validated through qPCR (FIG. 3B, FIG. 3C, FIG. 3D). They comprise Ifi44 (interferon-induced protein 44), a protein-coding gene that plays a role in induced glia inflammation, DNA-damage and degeneration (Pachiappan A. et al., Toxicon 2005; 46(8)); HPGD—hydroxyprostaglandin dehydrogenases are potent mediators of several biological processes, including inflammation and oxidative stress (Nakao R. et al., Chronobiol Int 2015; 32(4)); Casp4 that is known to be part of the apoptotic cascade (the gene is historically known as Casp11) (Villani G R et al., J Neurosci Res 2007; 85(3)); Ndst4, IL33, Dgkk and others that are involved always in inflammatory and oxidative stress pathways, but not included in the validation list (Table 2). This same set of genes was tested in MT-INCL mice at intermediate disease stage (FIG. 3B, FIG. 3C, FIG. 3D) and was shown to be similarly down-regulated versus INCL samples.

TABLE 2

| | Differentially expressed genes in MT-GLD vs GLD brains | |
|---|---|---|
| Gene Symbol | p-value (MT-GLD vs. GLD) | Fold-Change (MT-GLD vs. GLD) |
| Ndst4 | 0.000 | −3.089 |
| Tubb2b | 0.000 | −2.022 |

TABLE 2-continued

Differentially expressed genes in MT-GLD vs GLD brains

| Gene Symbol | p-value (MT-GLD vs. GLD) | Fold-Change (MT-GLD vs. GLD) |
| --- | --- | --- |
| Meis2 | 0.001 | −2.532 |
| Slc17a6 | 0.001 | −5.600 |
| Ifi44 | 0.002 | −2.553 |
| Il33 | 0.002 | −2.351 |
| Hpgd | 0.002 | −2.241 |
| Calca | 0.002 | −2.274 |
| P4ha3 | 0.002 | −2.684 |
| Thbs2 | 0.002 | −2.025 |
| Chrm2 | 0.002 | −2.792 |
| Zcchc12 | 0.002 | −2.826 |
| Htr2c | 0.003 | −3.387 |
| Zfp125 | 0.003 | −2.301 |
| AW551984 | 0.003 | −3.182 |
| Dok6 | 0.003 | −2.074 |
| Cdh19 | 0.003 | −2.798 |
| Zkscan16 | 0.003 | −2.273 |
| Slc18a2 | 0.003 | −2.908 |
| Rasgrf2 | 0.004 | −4.514 |
| Sprr1a | 0.004 | −2.545 |
| Kcnh5 | 0.004 | −3.612 |
| Gbp7 | 0.005 | −2.087 |
| Tac1 | 0.005 | −2.936 |
| Slitrk6 | 0.005 | −2.961 |
| Gm10944 | 0.005 | 2.703 |
| Mki67 | 0.005 | −2.075 |
| Kcnc2 | 0.005 | −2.645 |
| Mt1 | 0.005 | 2.327 |
| Frmpd3 | 0.005 | −2.091 |
| Gfap | 0.005 | −2.150 |
| Zfhx3 | 0.005 | −2.093 |
| Tacr1 | 0.006 | −2.193 |
| Mir1912 | 0.006 | −2.285 |
| Gpr165 | 0.006 | −2.451 |
| Casp4 | 0.006 | −2.752 |
| Tmem196 | 0.006 | −2.050 |
| Mit1 | 0.007 | −2.800 |
| Asah2 | 0.007 | −2.258 |
| Cntnap5a | 0.007 | −2.326 |
| Arhgap36 | 0.007 | −3.479 |
| Dgkk | 0.007 | −3.594 |
| Vwc2I | 0.008 | −3.608 |
| Tacr3 | 0.008 | −2.306 |
| RMST_7 | 0.008 | −2.526 |
| Rbp1 | 0.008 | −2.005 |
| Cbln2 | 0.008 | −2.349 |
| Lrrc55 | 0.009 | −2.149 |
| Tekt5 | 0.009 | −2.183 |
| Fxyd7 | 0.009 | −3.019 |
| Slit2 | 0.009 | −2.181 |
| Gabra5 | 0.009 | −5.903 |
| Pcdh7 | 0.009 | −2.041 |
| Shox2 | 0.010 | −2.013 |

To further explore the ability of MTs to mitigate oxidative stress in the disclosed models nitrotyrosine was measured, a marker of cell damage, inflammation, and nitric oxide production, in the brain of MT-GLD and control mice through immunofluorescence (FIGS. 3E and 3F) (Hidalgo J. et al., Exp Biol Med (Maywood) 2006; 231(9)). Nitrotyrosine signal was significantly and extensively reduced in many regions of MT-GLD brain (cerebellum, corpus callosum, brainstem) as compared to naïve GLD animals (FIGS. 3E and 3F). MT-GLD brain cells also showed a tendency towards ROS reduction when stained for DCFDA (DCFDA 6-carboxy-2',7'-dichlorodihydrofluorescein diacetate) (FIG. 3G).

Example 4: Purkinje Cell Loss is Rescued in MT-GLD and MT-INCL Mice

Figure 4:
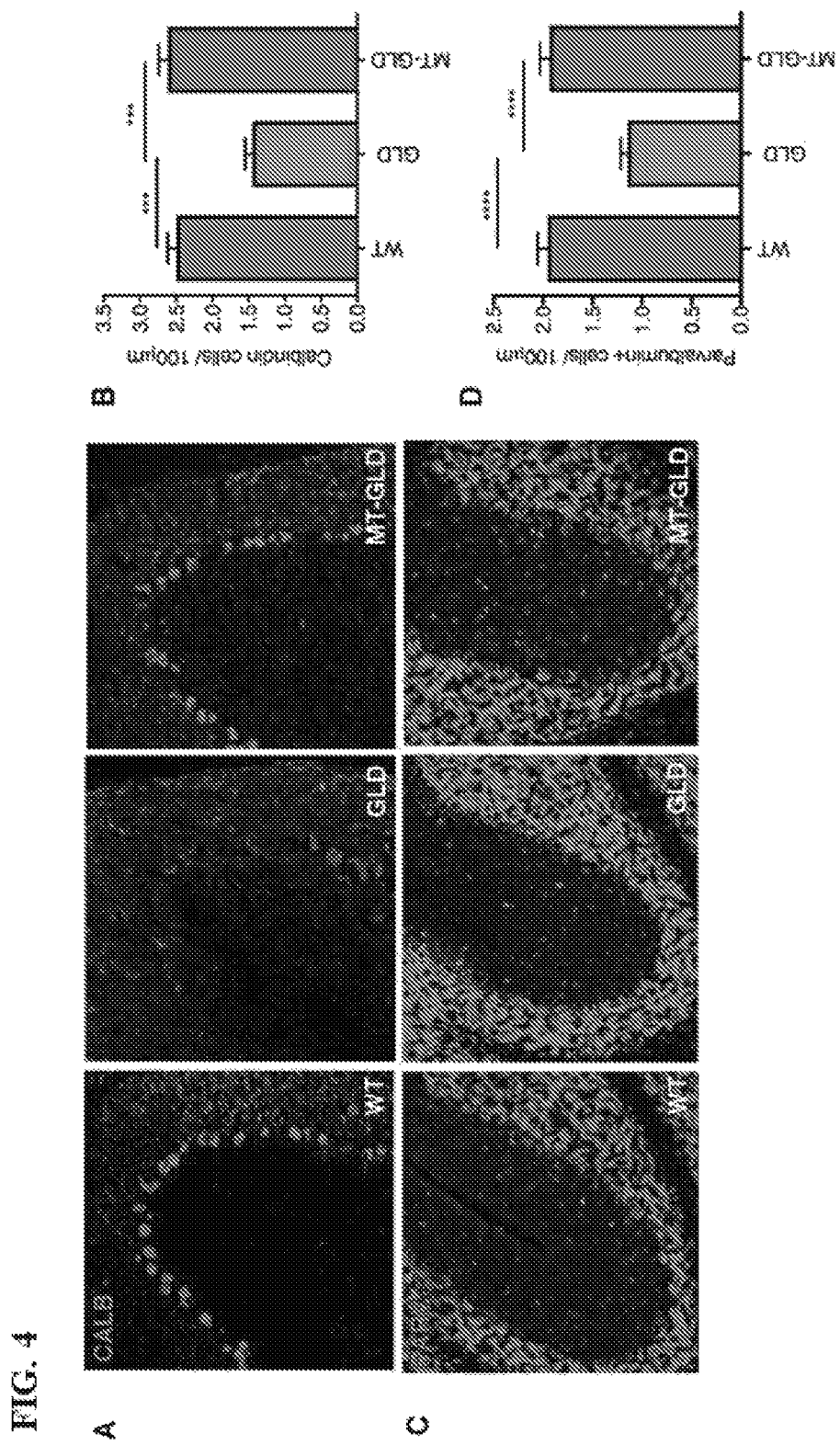
FIG. 4A, FIG. 4B, FIG. 4C, FIG. 4D, FIG. 4E, FIG. 4F, FIG. 4G, and FIG. 4H show Purkinje cell loss is rescued in both MT-GLD and MT-INCL models.
Figure 4:
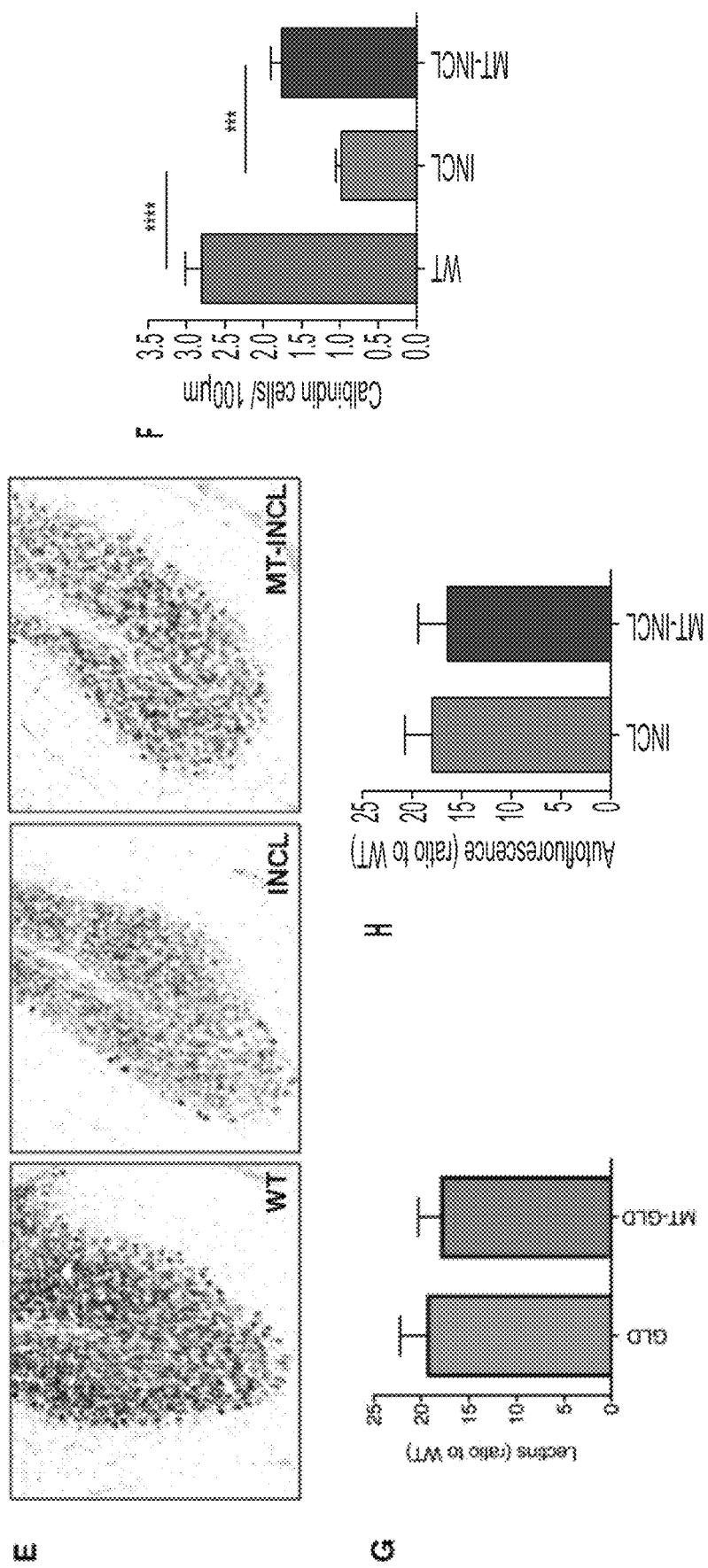

Purkinje cell loss is known to contribute to the severe and complex phenotype of GLD, phenomenon that is known to be strictly linked to apoptosis (Lin D S et al Gene 2015; 571(1)). It was confirmed that Purkinje cells are progressively lost from an early symptomatic to frankly symptomatic stage in GLD mice. Importantly, prevention of Purkinje cell loss was observed in the brain of MT-GLD mice (FIG. 4A and FIG. 4B). This rescue was demonstrated through both qualitative and quantitative measures of Calbindin Parvalbumin signals on GLD and MT-GLD cerebellum slices obtained at advanced disease stage (FIG. 4C and FIG. 4D).

Profound cerebellar pathology is also present in INCL mice (Macauley S L. et al., Exp Neurol 2009; 217(1)), consistent with the human course of the disease, with degenerating Purkinje cell bodies and dendritic arborizations representing early neuronal loss. Prevention of Purkinje cell degeneration and loss were also observed in the brain of MT-INCL mice already at intermediate disease stage (200 days), suggesting a specific effect of MTs on this neuronal compartment (FIG. 4E and FIG. 4F).

Example 5: Metallothionein Over-Expression is Not Impacting Primary Disease Defects MT over-expression was here shown to modulate secondary disease aspects of the two LSD models analyzed. For both models, however, the primary disease mechanism is represented by accumulation of storage material due to the disease-causing lysosomal hydrolase defect. Despite we did not expect this to happen, we anyhow assessed whether MTs could have any impact on the storage of undegraded substrates. As expected, MTs were not significantly affecting intracellular galactolipid storage in all brain regions analyzed in MT-GLD animals (FIG. 4G). Also in the MT-INCL model we did not observe any changes in the accumulation of autofluorescent storage material in the experimental groups analyzed by flow cytometry and immunofluorescence analysis (FIG. 4H).

Figure 5:
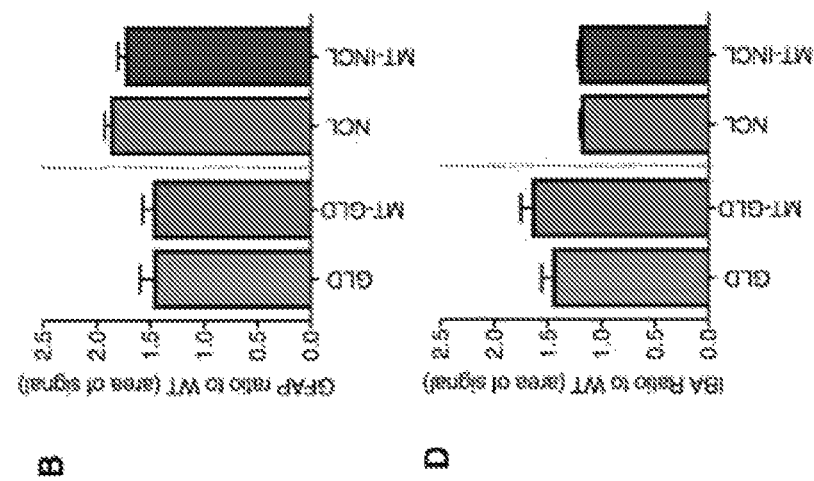
FIG. 5A, FIG. 5B, FIG. 5C, FIG. 5D, FIG. 5E, FIG. 5F, FIG. 5G, FIG. 5H, FIG. 5I, FIG. 5J, and FIG. 5K show MTs induce an anti-inflammatory M2-like microglia phenotype in GLD and INCL.
Figure 5:
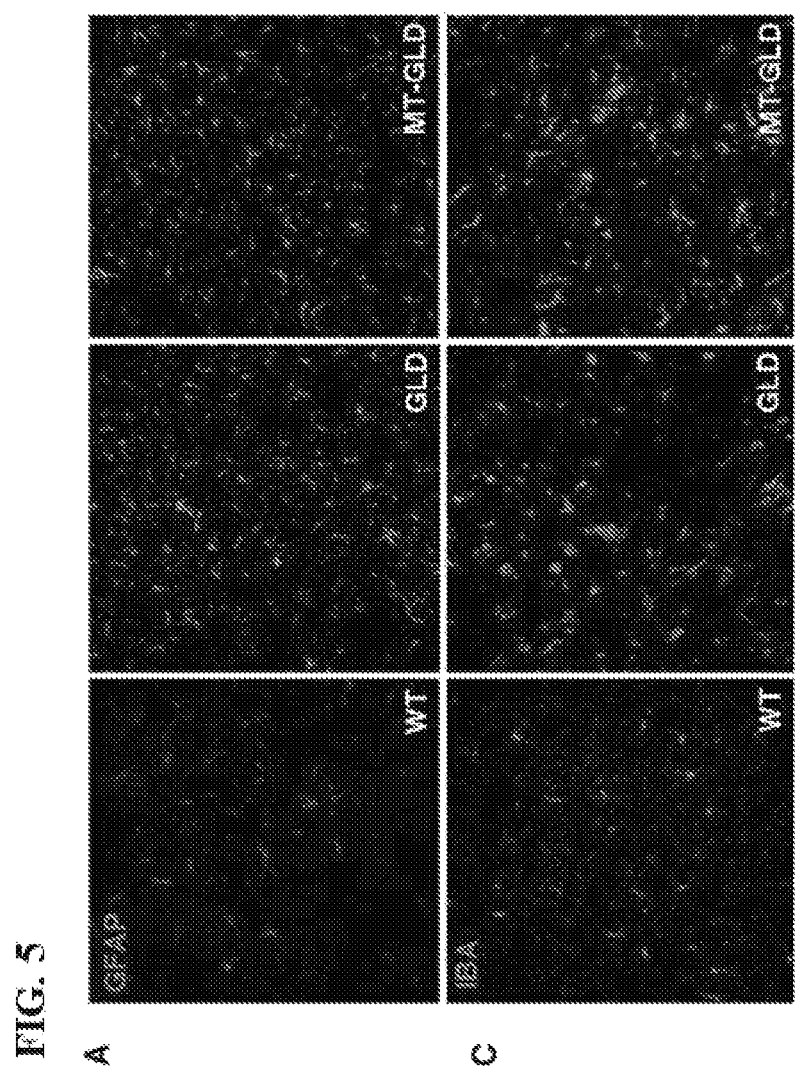
Figure 5:
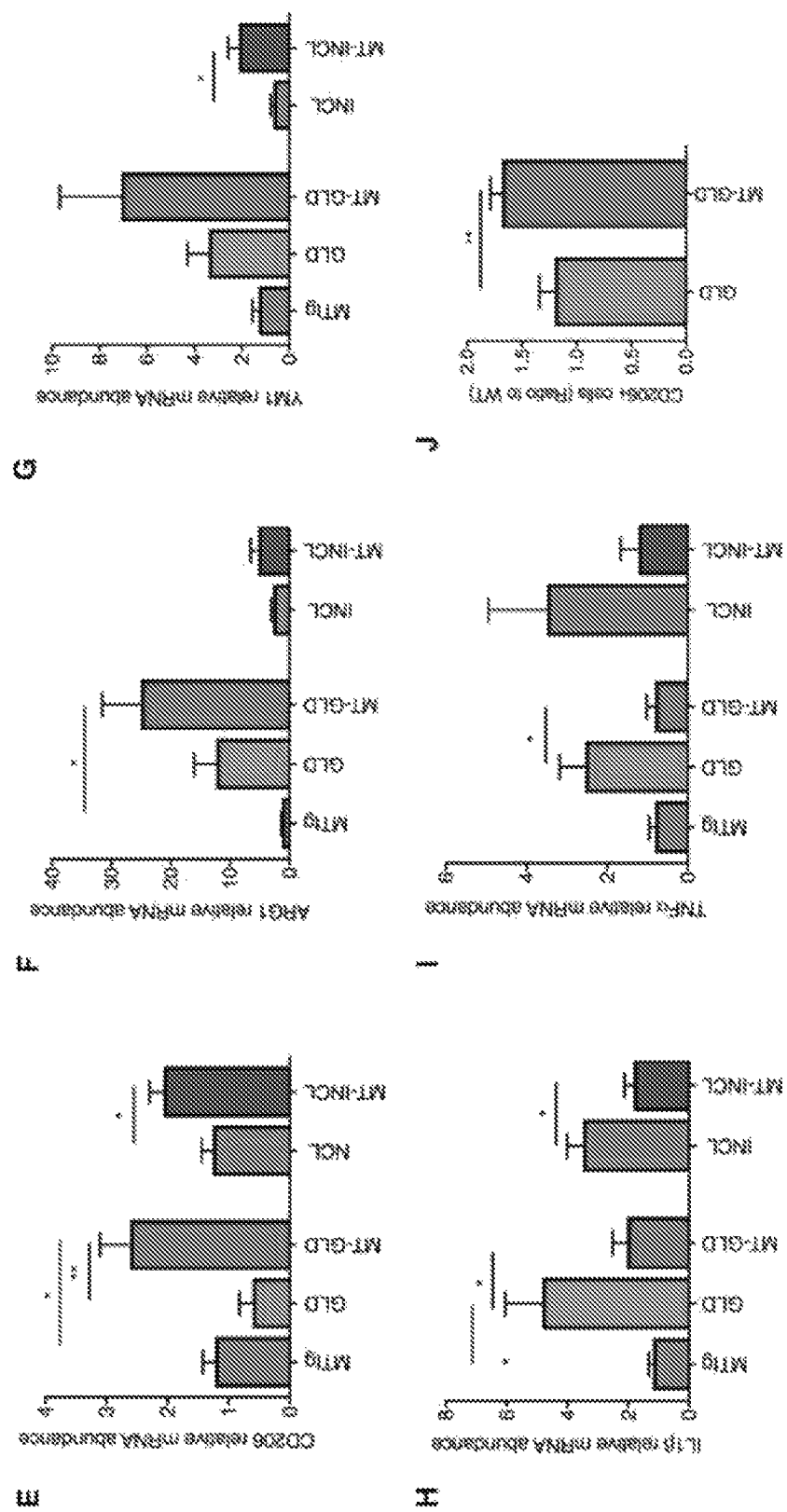
Figure 5:
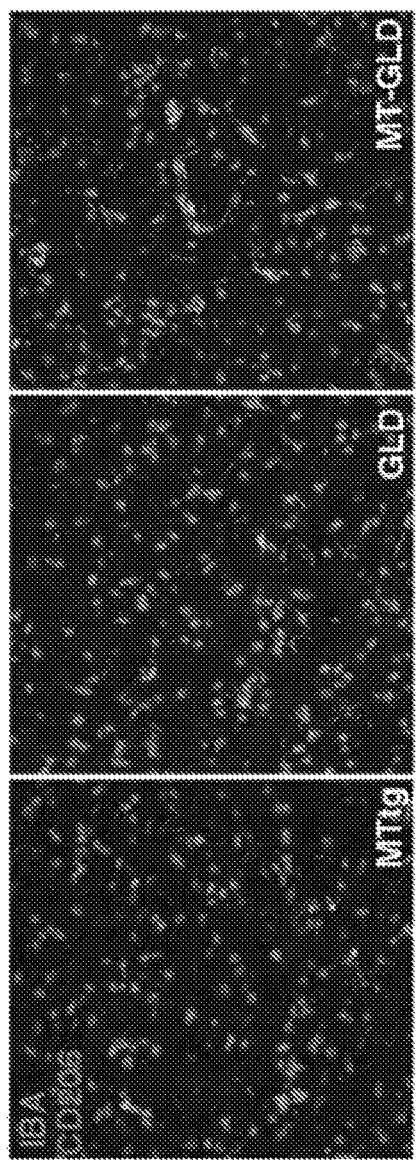

Example 6: Metallothioneins Induce an Anti-Inflammatory M2-Like Microglia Phenotype in GLD and INCL Next it was explored whether MTs could affect neuroinflammation in GLD and INCL mice. Immunofluorescence for astrocyte and microglia markers revealed similar levels of astrogliosis and microgliosis in MT-LSD mice and naïve LSD animals analysed at intermediate (MT-INCL and INCL) and advanced (PND36, MT-GLD and GLD) disease stage (FIG. 5A, FIG. 5B, FIG. 5C, FIG. 5D), indicating that MTs, despite being mostly produced by the astrocytes, may not be able to affect the phenotype of these cells. To further explore neuroinflammation in our models, myeloid cells/microglia populations were isolated from MT-GLD and control mouse brains and quantified mRNA levels of some well-known markers of microglia activation in these samples. Interesting, a significant increase in the expression of the anti-inflammatory markers Arginase1, CD206 and YM1 (also referred as M2 myeloid cell markers) was detected in the MT-GLD and MT-INCL cells over control GLD and INCL samples (FIG. 5E, FIG. 5F, FIG. 5G). Moreover, a decrease of the pro-inflammatory cytokines IL1β and TNFα was observed, which are produced by activated microglia cells (also referred as M1 myeloid cell markers), in MT-LSD samples versus naïve LSD controls (FIG. 5H and FIG. 5I). The levels of expression of these molecules in samples from MTtg mice were instead similar to WT controls, suggesting that the effect was present exclusively in the disease context. The expression of the CD206 receptor, a C-type lectin carbohydrate binding protein associated with M2 phenotype (Perego C. et al., J Neuroinflammation 2011; 8: 174), was also confirmed on MT-GLD brain sections analysed by immunofluorescence (FIG. 5J and FIG. 5K). CD206 positive area of signal was increased in MT-GLD mice brain myeloid cells as compared to naïve GLD animals.

Overall, these data suggest that MTs induce a skewing of microglia towards a M2-like anti-inflammatory status and thus the establishment of a neuroprotective environment that could counteract disease progression.

Figure 6:
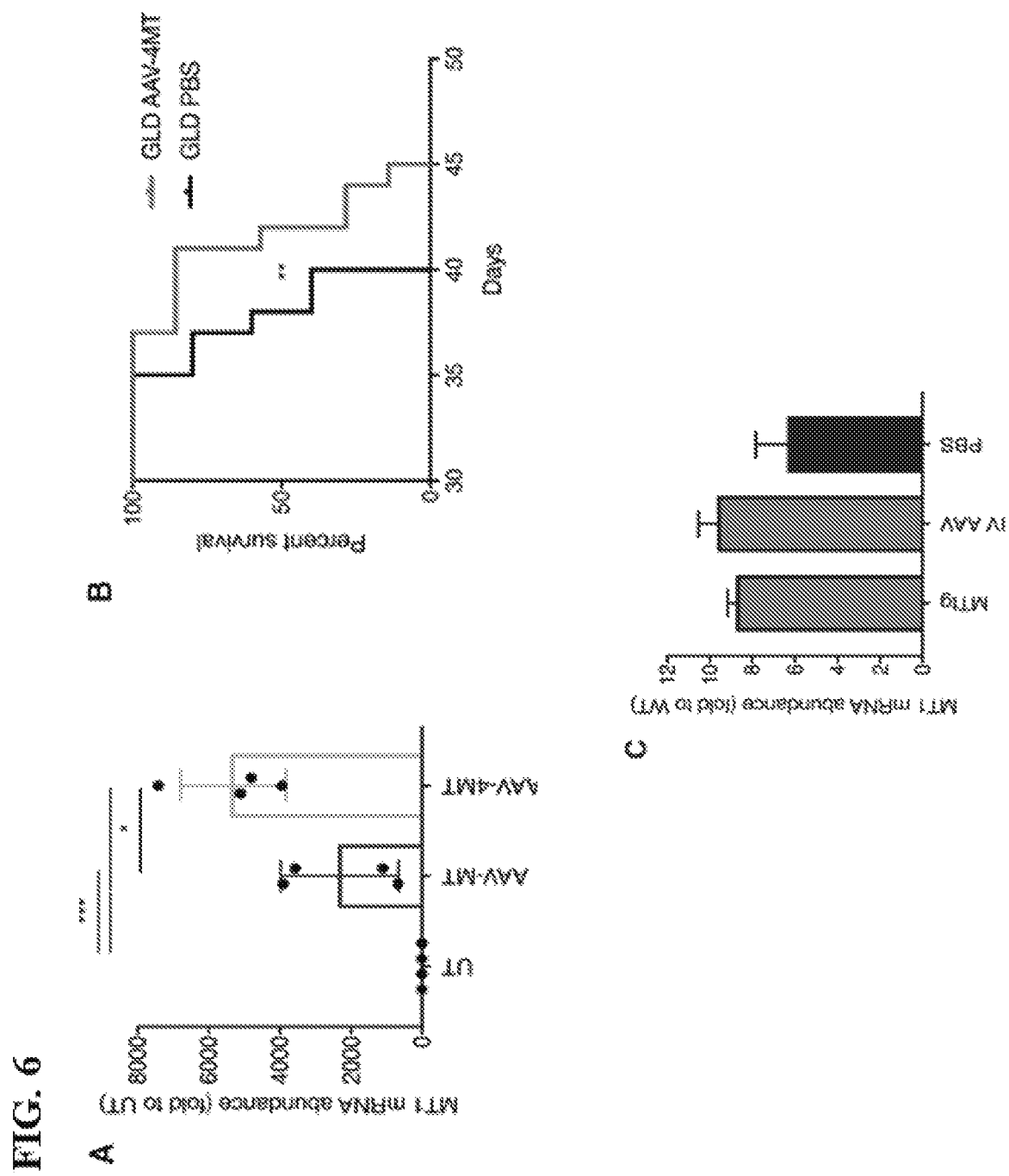
FIG. 6A, FIG. 6B, FIG. 6C, FIG. 6D, FIG. 6E, FIG. 6F, and FIG. 6G show MT delivery by AAV-PHP.B vectors ameliorates the GLD phenotype.
Figure 6:
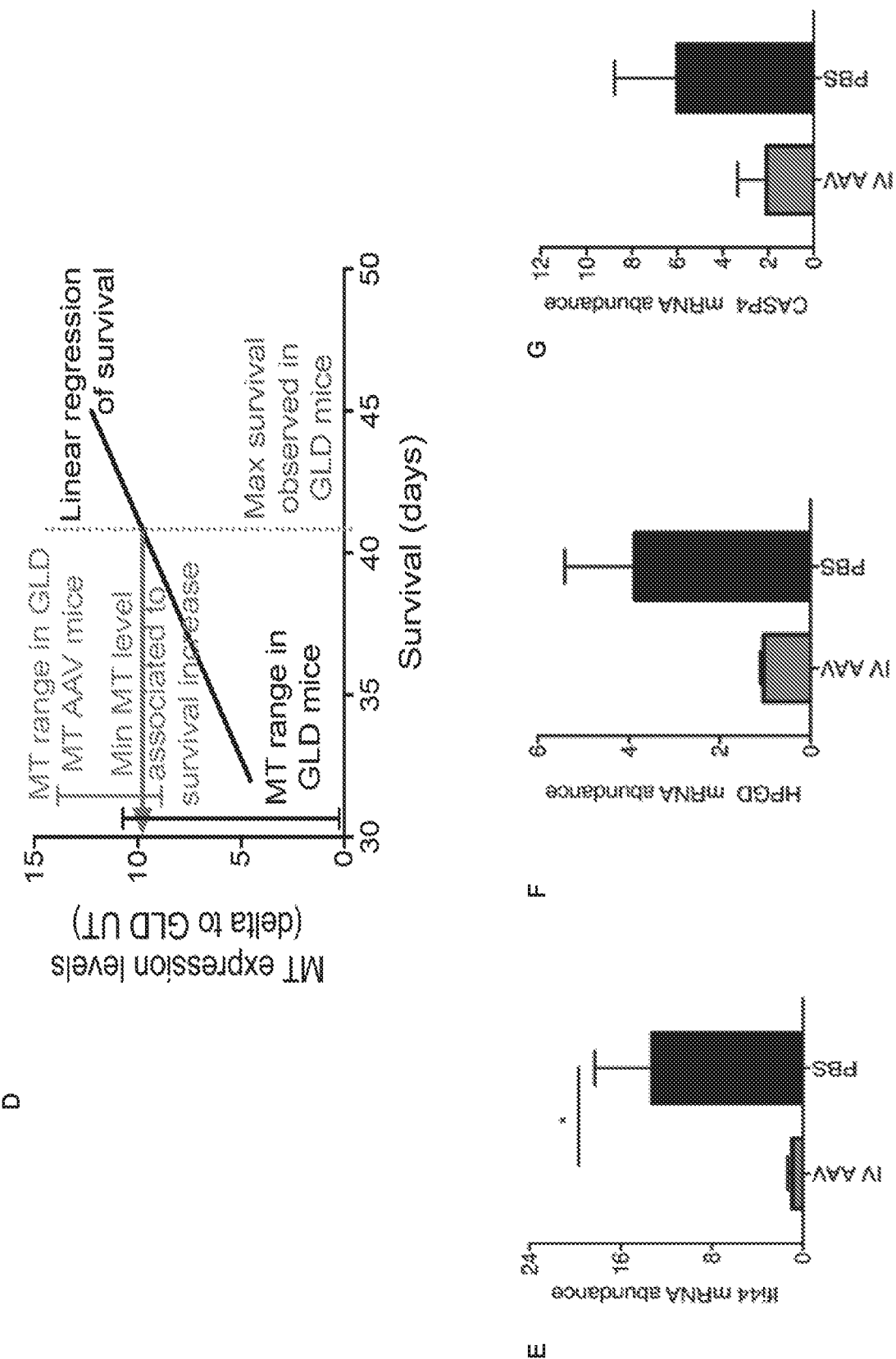

Example 7: Metallothioneins Delivery by AAV Vectors Ameliorates the GLD Phenotype As disclosed herein, the data on the constitutive overexpression of MT-1 in MT-LSD transgenic mice suggest that MTs could be exploited as neuroprotective agents for therapeutic purposes in LSDs. Thus a simple proof of concept experiment was performed injecting GLD mice with an MT-1 expressing adeno associated virus (AAV) vector produced with AAV-PHP.B, which is a recently developed capsid capable of high efficiency systemic CNS gene delivery in adult mice (Deverman B E et al., Nat Biotechnol 2016; 34(2): 204-9). AAV vectors carrying either one or four copies of the MT-1 cDNA in HEK-293 cells were compared, and as expected the latter vector resulted in higher MT-1 expression levels (FIG. 6A). We thus chose the AAV-4MT vector for in vivo studies. Two-day old (PND2) GLD mice were injected systemically with $2 \times 10^{10}$ vg of AAV-4MT vector and then monitored until the terminal stage. Interestingly, there was a significant increase in the survival of AAV treated mice as compared to GLD mice injected with PBS (FIG. 6B), consistent to what observed in the MT-GLD transgenic animals. This increased survival was paralleled by an increased MT-1 quantification in the brain of the AAV-injected animals over controls (FIG. 6C). Also in this case MT expression levels versus survival were plotted for both PBS and AAV-injected mice in the attempt to identify therapeutic target levels for MT exogenous delivery (FIG. 6D). Interestingly, the minimum fold increase associated to a gain in survival was of 3.3 folds over basal GLD-associated MT transcript levels, in a range consistent with what observed in the MT-LSD models. Importantly, survival gain was associated to the down-regulation of inflammation, oxidative stress, and apoptosis genes in the AAV treated mice, as observed in MT-GLD mice (FIG. 6E, FIG. 6F, FIG. 6G), Without being bound by theory, this indicates that MTs were affecting the same pathway regulation mediated also upon exogenous AAV-mediated delivery.

MTs were previously identified and characterized as biomarkers of brain disease that dynamically modify their expression in the course of disease progression and response to treatment in a variety of LSDs (Cesani M. et al., Ann Neurol 2014; 75(1): 127-137). MTs could exert a protective role in the diseased brain, since their expression levels in astrocytes increase upon administration of anti-inflammatory drugs. MTs were shown to have neuroprotective capacities in acute brain damage (West A K et al., Neurotoxicology 2008; 29(3)) and more recently in chronic diseases, as Parkinson's disease (Ebadi M H et al., Brain Res Mol Brain Res 2005; 134(1)), Amyotrophic Lateral Sclerosis (Tokuda E. et al., Hum Mol Genet 2014; 23(5)); and Alzheimer's disease (Manso Y. et al., J Alzheimers Dis 2016; 51(1)). Based on these indications, the possibility of exploiting MTs to exert neuroprotection in LSDs characterized by severe neurologic involvement was explored.

MTs are described to exert anti-oxidant, anti-inflammatory and anti-apoptotic functions in the diseased brain, but little is known about MT-activated pathways and their mechanisms of action in this compartment (Ito Y. et al., Curr Pharm Biotechnol 2013; 14(4)). Experimental evidences support the hypothesis that MTs, synthesized from astrocytes in the diseased brain upon pro-inflammatory and pro-oxidative stimuli, can be up-taken by neurons through the receptor Lrp2/Megalin and then exert their detoxifying activity (Chung R S et al., J Biol Chem 2008; 283(22)), mostly in the context of neuronal damage. Interestingly, increased levels not only of MTs, but also of Lrp2 were documented in human brain LSD samples and in murine LSD brain samples, and particularly in diseases with neuronal involvement like NCL. Thus, in an attempt to assess the beneficial effects of MTs in the LSD brain, if any, and the role of the MT-Lrp2 axis in vivo, MTtg over-expressing mice were cross-bred with the INCL mouse model. Interestingly, MT constitutive expression ameliorated the INCL phenotype in the MTtg disease model. The improved phenotype and increased survival of MT-INCL mice supported the initial hypothesis and the role of MTs (and Lrp2) in this disease setting. Importantly, a similar beneficial effect of MTs was also observed in the extremely severe GLD animal model of which survival was also improved. These results are positively surprising being solely depending on MT addition, in the absence of any therapeutic intervention targeting the primary lysosomal enzyme deficiency causing the disease. Notably, relatively little increase of MT expression levels in addition to the natural occurring over-expression associated to the primary disease was sufficient to determine benefitical effects and a survival gain in both tested animal models.

Importantly, survival gain was accompanied by consistent transcriptional/expression changes observed in the MT-LSD brains. These changes were represented by a modulation of neuroinflammation, microglia activation and oxidative stress, and neuronal protection, at least at the examined sites. A profound and specific effect was observed on Purkinje cells that were abundantly rescued from degeneration and apoptosis in both models. Many in vitro studies have shown that MT can exert neuroprotection in both neuronal and cerebellar granule neuron cell culture systems, meaning attributable to all neuronal cell types (Ambjorn M. et al., J Neurochem 2008; 104(1)). Mechanisms of neuronal protection in the Purkinje cell layer and overall phenotype amelioration may involve many of the MT well known mechanisms of action.

One of the most striking effects of MTs is the reduction of oxidative stress and related pathways, as it was shown in a mouse model of dystrophinopathy(Di Foggia V. et al., J Exp Med 2014; 211(13)). It is also widely accepted that a dysregulation of different pathways involved in oxidative stress responses and inflammation occurs in LSDs as consequence of a block of autophagy (Settembre C. et al., Nat Rev Mol Cell Biol 2013; 14(5)). Finally, MTs were shown to protect against oxidative stress-induced lysosomal destabilization (Baird S K. et al., Biochem J 2006; 394(Pt 1)). Based on these evidences and the data disclosed herein, MT could be over-expressed in response to oxidative stress and inflammation caused by lysosomal dysfunction. Thus, the therapeutic effects exerted by MTs in the LSD models could be mediated by their ability to modulate these events. Indeed, measurements performed in our models indicate that MTs can down-modulate and mitigate oxidative stress associated to lysosomal dysfunction, being potentially beneficial to the damaged Purkinje layer.

Moreover, despite macroscopic measurements that failed to demonstrate a MT effect on astrocytosis and microgliosis in the disease models, on closer observation a change was detected in the phenotype of microglia that acquired M2-like markers (with an increase in Arginase1 and CD206 expression) and down-regulated IL1β and TNFα expression in both the MT-LSD models. This increase of alternatively activated M2-like microglia markers as compared to classical M1-like pro-inflammatory ones indicates that a reshaping of microglia phenotype, and possibly their functions, away from inflammation and towards neuroprotection, occurred when MTs were over-expressed in the LSD setting. Emerging data support the relevance of the M1/M2 paradigm in neurodegenerative diseases and more in the GLD setting (Nicaise A M et al., J Neurosci Res 2016; 94(11)). The possible impact of MTs on the M1/M2 balance in the MTtg-LSD brains is also further confirmed by the evidence of a reduction of oxidative stress in microglia cells from MT-GLD mice, which are endowed with M2 features, phenomenon that is widely described in literature (Rojo A I. et al., Antioxid Redox Signal 2014; 21(12)). Notably, the involvement of microglia in mediating MT-driven neuroprotection is reported here for the first time.

Another aspect that could be of relevance in interpreting the findings disclosed herein, particularly in the INCL model, is the recent evidence of biometal deregulation in different NCL mouse models. In fact, altered biometal homeostasis was identified in three different animal models of NCL, including INCL, which showed significant accumulation of the biometals zinc, copper, manganese, iron and cobalt. Patterns of biometal accumulation in each model preceded significant neurodegeneration, and paralleled the relative severity of disease known for each model40. It was similarly hypothesized that MTs are playing a protective role in ALS disease course potentially related to normalization of copper dyshomeostasis within astrocytes, promoting survival of motor neurons (Tokuda E. et al., Hum Mol Genet 2014; 23(5)). Similar disease mechanisms could occur in the LSD context, but have still not yet been explored.

Overall, these data may indicate that exogenously delivered MTs could exert a therapeutic role in LSDs severely affecting the CNS by modulating disease-related mechanisms of neural damage. However, the artificial nature of the models employed where MTs were constitutively expressed at very high levels upon trans-genesis may not allow faithfully predicting clinical transferability of our findings. We thus addressed this limitation by performing a simple proof of concept study intended at assessing the feasibility and therapeutic relevance of MT delivery to LSD mice, and prospectively LSD patients. Recently, the newly developed AAV-PHP.B capsid was shown to mediate high efficiency widespread CNS gene transfer upon intravascular administration in adult mice (Deverman B E. et al., Nat Biotechnol 2016; 34(2)). Thus, as disclosed herein, AAV-PHP.B vectors were generated containing one or four MT copies linked by three different 2A peptides, and confirmed the greater performance of the expression system with four copies in driving increased MT expression both at the RNA and protein levels. When injected in vivo in GLD animals this AAV-4MT vector reproduced and validated the findings observed in MTtg-GLD mice. Indeed, AAV-mediated delivery of MT-1 cDNA and its expression in the affected GLD brain exerted similar effects as constitutive expression by transgenesis, with significantly improved survival, modulation of inflammation and oxidative stress, and anti-apoptotic effects exerted in the GLD central nervous system. These findings thus validate the concept that MTs could be further explored as therapeutic agents in LSDs.

In conclusion, the neuroprotective features described so far are promising for exploiting MTs as novel therapeutic agents and/or targets for LSDs. MT supplementation therapy is envisaged in any form available in terms of clinical translation as a neuroprotective strategy that may be eventually coupled with other approaches aiming at enzyme activity reconstitution.

The results described herein above, were obtained using the following methods and materials.

Human Studies

Post-mortem snap-frozen and formalin-fixed human brain samples from patients affected by LSD (Globoid Cell Leukodystrophy—GLD n=2, Metachromatic Leukodystrophy—MLD n=2, NCL n=2, Niemann Pick disease—NPC n=2) and from 4 age- and sex-matched controls were obtained from the NICHD Brain and Tissue Bank for Developmental Disorders at University of Maryland, Baltimore. Temporal gap between death and tissue sampling was inferior to 24 hours for every sample. RNA extraction was performed as already described in our previous study (Cesani et al., 2014). For immuno-histochemical analysis, the MT clone E9 (Dako) was employed at 1:1000 dilution. For Lrp2 mRNA quantification the Taqman assay Hs00189741_m1 was used. Western blot was performed with a primary rabbit antibody α-Lrp2 (from Abcam) used at 1:1000 (see e.g. Cesani et al., 2014).

Mouse Studies

All procedures were approved by the Animal Care and Use Committees of the Fondazione San Raffaele del Monte Tabor (IACUC 573) and of The Dana Farber Cancer Institute Committee on Animals (IACUC 15-024 and 15-042). Murine MT1 levels were measured in the following LSD mouse models: GLD (n=6 at 40 days), MLD (n=4 at 10 months), Sandhoff (SD, n=4, 3.5 months), infantile NCL (INCL, n=4 at 200 days), Mucopolysaccharidosis type I (MPS I, n=4 at 10 months), MPS II (n=3 at 10 months), MPS III (n=4 at 40 days), Multiple Sulfatase Deficiency (MSD, n=5 at 2-3 weeks), compared to 20 wild type (WT) mice at different ages.

Transgenic mice harboring murine MT-1 (strain B6.Cg-Tg(Mt1)174Bri/J, stock number 002210) were purchased from the Jackson Laboratory. MT-1 mice were maintained on a C57BL/6J background. Heterozygous GLD mice were crossed with hemizygous MT-1. Then starting from the second generation, double transgenic mice affected by GLD pathology (homozygous defective mutant mice) carrying MT-1 were obtained. The same strategy was applied to INCL mouse model. INCL mice were scored for disease progression according to symptom appearance by using a validated disease severity score (extensively described in Peviani et al., Hematopoietic cell transplantation can mitigate neuronal pathology in a mouse model of infantile neuronal ceroid lipofuscinosis, submitted).

Immunofluorescence and IHC studies. 36-day-old GLD, MT-GLD mice and age-matched WT mice, 200-days-old INCL, MT-INCL and age-matched WT mice were sacrificed under deep anesthesia and perfused with Phosphate-buffer saline (PBS). Brains were isolated and fixed for 16 hours in 4% paraformaldehyde, equilibrated in 10-30% sucrose gradient in PBS for 48 hours and then embedded in OCT compound for quick freezing. 16-micron cryostat sections were incubated overnight at 4° C. with primary antibodies: mouse monoclonal to Metallothionein (DAKO) 1:100; rabbit anti-glial fibrillary acidic protein (GFAP) (MCA1909; Serotec Ltd) 1:500; rabbit anti-Ibal (Wako) 1:100, mouse monoclonal anti-Nitrotyrosine (Abcam) 1:500; rat anti-mouse CD206 (AbD Serotec) 1:200; rabbit anti-Calbindin (Swant) 1:700; rabbit anti-Parvalbumin (Swant) 1:700; then for 1 hour 30 minutes at RT with secondary antibodies: goat anti-mouse Alexa Fluor488 1:1000; rabbit anti-goat Alexa Fluor488 1:1000, goat anti-rabbit AlexaFluor546 1:1000, goat anti-mouse AlexaFluor546 1:1000 (Molecular Probes). Samples were visualized with Zeiss Axioskop2 microscope and a 3-laser confocal microscope (Radiance 2100; BioRad TCS SP2)—fluorescent signals from single optical sections were sequentially acquired using constant settings for each channel, defined based on the negative staining control. Cryostat sections were also processed for lectin histochemistry, following previously described methods for staining and counting (Visigali et al., Neurobiol Dis 2009; 34(1): 51-62; Neri et al., Stem Cells 2011; 29(10): 1559-1571). Immunoistochemistry with DAB (3,3'-diaminobenzidine) and cresyl violet were performed as previously described (Peviani et al., Neurobiol Dis 2014; 62: 218-32). For computer aided image analysis, ImageJ software was used to quantify the extension of signal positive area on confocal images (total signal positive area). For proper comparison, slices to be compared for signal quantification were stained and images were acquired simultaneously.

Sorting of microglia populations. Brains after perfusion were processed as described (Capotondo et al., Intra-cerebral ventricular delivery of hematopoietic stem and progenitor cells allows efficiently generating microglia-like cells in myeloablated recipients).

DCFDA assay. Levels of intracellular reactive oxygen species (ROS) were determined from the change in fluorescence resulting from oxidation of the fluorescent probe H2DCFDA. Briefly, myeloid cells isolated by Percoll selection were washed once with FBS-free DMEM and incubated in a 50 μM solution of the fluorescent probe H2DCFDA for 1 h at 37° C. The cells were then washed twice with FBS-free medium, and fluorescence corresponding to intracellular ROS was analyzed at flow cytometry in FITC channel (LSR Fortessa).

RNA extraction. RNA from sorted microglia was extracted with RNeasy plus Micro Kits (Qiagen), RNA from cerebella (200 μg) used for Whole Transcriptome Assay was extracted with RNeasy Lipid Tissue Mini Kit and treated with DNase I (Qiagen). Quantitative PCR was performed for the following genes: MT1 Mm00496660_g1, IL1β Mm00434228_m1, TNFα Mm00443258_m1, Ifi44 Mm00505670_m1, Arginase Mm00477592_m1, CD206 Mm01329362_m1, YM1 Mm00657889_mH, Hpgd Mm00515121_m1, Casp4 Mm004323 04m1.

Whole transcriptome analysis. Total RNA was extracted from cerebella of 36-day-old GLD mice (n=3), MT-GLD mice (n=3) at the same age, age-matched WT mice (n=3) and MTtg over-expressing mice (n=3). The quality of total RNA was first assessed using an Agilent Bioanalyzer 2100 (Agilent Technologies, Palo Alto, Calif.). Biotin-labeled cDNA targets were synthesized starting from 150 ng of total RNA. Double stranded cDNA synthesis and related cRNA was performed with GeneChip® WT Plus Kit (Affymetrix, Santa Clara, Calif.). The sense strand cDNA was synthesized with the same kit and then fragmented and labelled. DNA microarray hybridization and image acquisition, processing and bioinformatics analysis were performed. Hybridization was performed using the GeneChip® Hybridization, Wash and Stain Kit that contains mix for target dilution, DMSO at a final concentration of 7% and pre-mixed biotin-labelled control oligo B2 and bioB, bioC, bioD and cre controls (Affymetrix cat #900299) at a final concentration of 50 pM, 1.5 pM, 5 pM, 25 pM and 100 pM, respectively. Targets were diluted in hybridization buffer at a concentration of 25 ng/μl, denatured at 99° C. for 5 minutes, then incubated at 45° C. for 5 minutes and centrifuged. A single GeneChip® Mouse Transcriptome Array 1.0 was then hybridized with each biotin-labelled sense target.

Hybridizations were performed for 16 h at 45° C. in a rotisserie oven. GeneChip® cartridges were washed and stained with GeneChip®. Hybridization, Wash and Stain Kit in the Affymetrix Fluidics Station 450 following the FS450_0002 standard protocol, including the following steps: (1) (wash) 10 cycles of 2 mixes/cycle with Wash Buffer A at 30° C.; (2) (wash) 6 cycles of 15 mixes/cycle with Wash Buffer B at 50° C.; (3) stain of the probe array for 5 min in SAPE solution at 35° C.; (4) (wash) 10 cycles of 4 mixes/cycle with Wash Buffer A at 30° C.; (5) stain of the probe array for 5 min in antibody solution at 35° C.; (6) stain of the probe array for 5 min in SAPE solution at 35° C.; (7) (final wash) 15 cycles of 4 mixes/cycle with Wash Buffer A at 35° C.; (8) fill the probe array with Array Holding buffer.

Image acquisition, processing and bio-informatic analysis. GeneChip arrays were scanned using an Affymetrix GeneChip® Scanner 3000 7G using default parameters. Affymetrix GeneChip® Command Console software (AGCC) was used to acquire GeneChip® images and generate .DAT and .CEL files, which were used for subsequent analysis with proprietary software.

Preclinical Studies Employing AAV-PHP.B Vector Encoding MT-1

A cassette encoding either one or four copies of MT-1 separated by 2A peptides was cloned in place of GFP in the AAV-CBA.GFP-Wpre plasmid. AAV-PHP.B vectors were produced by transient triple transfection of HEK-293 cells with transfer plasmid, Fd6 helper plasmid and a plasmid generated in the Sena-Esteves laboratory carrying AAV2 rep and the recently described AAV-PHP.B cap gene13. Vectors were purified by iodixanol gradient centrifugation followed by buffer exchange to phosphate buffered saline (PBS) using 7K MWCO Zeba Spin Desalting columns (Thermo Scientific) and finally concentrated with 100K Amicon Ultra-15 centrifugal filters (Merck Millipore, Cork, Ireland). Titers were determined by qPCR using primers and probes to the BGH polyadenylation signal. AAV vectors were injected via the superficial temporal vein of two-day old (PND2) GLD mice as described (Capotondo et al, 2017, submitted). Control mice received PBS.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related in part to U.S. Patent Application Ser. No. 62/408,693, the disclosures of which are hereby incorporated by reference in their entirety.

All patents, publications, and accession numbers mentioned in this specification are herein incorporated by reference to the same extent as if each independent patent, publication, and accession number was specifically and individually indicated to be incorporated by reference.

What is claimed is:

1. A method of treating a lysosomal storage disease or disorder in a subject, the method comprising increasing the level, expression, or activity of a metallothionein-1 polypeptide or polynucleotide in the subject relative to a reference by administering to the subject an adeno-associated virus (AAV) vector or a lentiviral (LV) vector encoding the metallothionein-1 polypeptide or polynucleotide, wherein the lysosomal storage disease is globoid leukodystrophy or metachromatic leukodystrophy.

2. The method of claim 1, wherein the subject is preselected by detecting an increase in the level of a metallothionein (MT) polynucleotide or polypeptide in a sample of the subject relative to a reference.

3. The method of claim 1, wherein the metallothionein is selected from the group consisting of metallothionein-1A (MT1A), metallothionein-1B (MT1B), metallothionein-1E (MT1E), metallothionein-1F (MT1F), metallothionein-1G (MT1G), metallothionein-1H (MT1H), metallothionein-lI pseudogene (MT1Ip or MTE), metallothionein-1L (LT1L or MT1R), metallothionem-1M (MT1M or MT1K), and metallothionein-1X (MT1X).

4. The method of claim 1, wherein the method comprises administering the AAV vector to the subject.

5. The method of claim 4, wherein the AAV vector is administered systemically.

6. The method of claim 1, wherein the method comprises administering the LV vector.

7. The method of claim 6, wherein the LV vector is administered systemically.

8. A method of treating a lysosomal storage disease or disorder in a subject, the method comprising increasing the level, expression, or activity of a metallothionein-1 polypeptide or polynucleotide in the subject relative to a reference by administering to the subject hematopoietic stem cells (HSCs) comprising a vector encoding the metallothionein-1 polypeptide or polynucleotide, wherein the lysosomal storage disease is globoid leukodystrophy or metachromatic leukodystrophy.

9. The method of claim 8, wherein the subject is preselected by detecting an increase in the level of a metallothionein (MT) polynucleotide or polypeptide in a sample of the subject relative to a reference.

10. The method of claim 8, wherein the metallothionein selected from the group consisting of metallothionein-1A (MT1A), metallothionein-1B (MT1B), metallothionein-1E (MT1E), metallothionein-1F (MT1F), metallothionein-1G (MT1G), metallothionein-1H (MT1H), metallothionein-lI pseudogene (MT1Ip or MTE), metallothionein-1L (LT1L or MT1R), metallothionem-1M (MT1M or MT1K), and metallothionein-1X (MT1X).

11. The method of claim 8, wherein the vector is a lentiviral vector or an adeno associated virus (AAV) vector.

* * * * *